US010803747B2

(12) United States Patent
DiMeo et al.

(10) Patent No.: US 10,803,747 B2
(45) Date of Patent: *Oct. 13, 2020

(54) PRESENTING GEOGRAPHIC SEARCH RESULTS USING LOCATION PROJECTION AND TIME WINDOWS

(71) Applicant: INRIX, INC., Kirkland, WA (US)

(72) Inventors: David DiMeo, NorthVille, MI (US); Andreas Hecht, Chicago, IL (US)

(73) Assignee: INRIX, Inc., Kirkland, WA (US)

(*) Notice: Subject to any disclaimer, the term of this patent is extended or adjusted under 35 U.S.C. 154(b) by 0 days.

This patent is subject to a terminal disclaimer.

(21) Appl. No.: 16/509,571

(22) Filed: Jul. 12, 2019

(65) Prior Publication Data
US 2019/0340926 A1 Nov. 7, 2019

Related U.S. Application Data

(63) Continuation of application No. 15/123,022, filed as application No. PCT/US2015/018440 on Mar. 3, 2015, now Pat. No. 10,354,527.
(Continued)

(51) Int. Cl.
B60W 40/00 (2006.01)
G08G 1/0967 (2006.01)
(Continued)

(52) U.S. Cl.
CPC ... *G08G 1/096791* (2013.01); *A61B 5/02055* (2013.01); *A61B 5/0476* (2013.01);
(Continued)

(58) Field of Classification Search
CPC ............ G02C 21/3484; G02C 21/3476; G02C 21/3682; G02C 21/3617; G02C 21/3655;
(Continued)

(56) References Cited

U.S. PATENT DOCUMENTS 6,317,686 B1 * 11/2001 Ran .................... G01C 21/3691
701/117
6,401,034 B1 * 6/2002 Kaplan .............. G01C 21/3476
340/988

(Continued)

OTHER PUBLICATIONS

EP Search Report cited in EP Application No. 15759116.5 dated Feb. 13, 2018.
(Continued)

*Primary Examiner* — Richard A Goldman
(74) *Attorney, Agent, or Firm* — Cooper Legal Group, LLC

(57) ABSTRACT

Users within transit in a vehicle may initiate location queries to fulfill a set of interests, such as stops for food, fuel, and lodging. A device may fulfill the queries according to various factors, such as the distance of nearby locations to the user or to another location specified by the user, and the popularity of various locations. However, the user may not have specified or even chosen a route, and may wish to have interests fulfilled at a later time (e.g., stopping for food in 30 minutes), and a presentation of search results near the user's current location may be unhelpful. Presented herein are techniques for fulfilling location queries that involve predicting a route of the user, and identifying a timing window for the query results (e.g., locations that are likely to be near the user's projected location when the wishes to stop for food in 30 minutes).

20 Claims, 12 Drawing Sheets

Related U.S. Application Data

(60) Provisional application No. 61/946,962, filed on Mar. 3, 2014.

(51) Int. Cl.

| | |
|---|---|
| H04W 4/50 | (2018.01) |
| G06N 20/00 | (2019.01) |
| G06F 16/29 | (2019.01) |
| H04W 4/024 | (2018.01) |
| H04W 4/029 | (2018.01) |
| G08G 1/01 | (2006.01) |
| B60W 40/08 | (2012.01) |
| B60W 40/09 | (2012.01) |
| G08G 1/09 | (2006.01) |
| G07B 15/06 | (2011.01) |
| G08G 1/0968 | (2006.01) |
| G08G 1/097 | (2006.01) |
| B60W 30/14 | (2006.01) |
| G05D 1/00 | (2006.01) |
| G07C 5/00 | (2006.01) |
| A61B 5/0205 | (2006.01) |
| A61B 5/0476 | (2006.01) |
| A61B 5/00 | (2006.01) |
| G05D 1/02 | (2020.01) |
| H04B 1/3822 | (2015.01) |
| H04L 29/08 | (2006.01) |
| B64C 39/02 | (2006.01) |
| H04B 7/185 | (2006.01) |
| G06Q 20/10 | (2012.01) |
| G06Q 30/02 | (2012.01) |
| H04W 12/08 | (2009.01) |
| H04M 15/00 | (2006.01) |
| G06Q 40/08 | (2012.01) |
| H04L 9/32 | (2006.01) |
| B60R 16/023 | (2006.01) |
| G07B 15/00 | (2011.01) |
| G08G 1/065 | (2006.01) |
| G01C 21/36 | (2006.01) |
| H04W 4/42 | (2018.01) |
| H04W 4/40 | (2018.01) |
| G01C 21/34 | (2006.01) |
| G08G 1/07 | (2006.01) |
| G08G 1/0962 | (2006.01) |
| G08G 1/0965 | (2006.01) |
| H04W 4/48 | (2018.01) |
| A61B 5/024 | (2006.01) |
| A61B 5/053 | (2006.01) |
| G06Q 50/30 | (2012.01) |

(52) U.S. Cl.
CPC ........ *A61B 5/4845* (2013.01); *B60R 16/0236* (2013.01); *B60W 30/143* (2013.01); *B60W 40/08* (2013.01); *B60W 40/09* (2013.01); *B64C 39/024* (2013.01); *G01C 21/3415* (2013.01); *G01C 21/3469* (2013.01); *G01C 21/3617* (2013.01); *G01C 21/3655* (2013.01); *G01C 21/3667* (2013.01); *G01C 21/3682* (2013.01); *G05D 1/0011* (2013.01); *G05D 1/0088* (2013.01); *G05D 1/021* (2013.01); *G06F 16/29* (2019.01); *G06N 20/00* (2019.01); *G06Q 20/102* (2013.01); *G06Q 30/0283* (2013.01); *G06Q 40/08* (2013.01); *G07B 15/00* (2013.01); *G07B 15/063* (2013.01); *G07C 5/008* (2013.01); *G08G 1/012* (2013.01); *G08G 1/0112* (2013.01); *G08G 1/0129* (2013.01); *G08G 1/0141* (2013.01); *G08G 1/0145* (2013.01); *G08G 1/065* (2013.01); *G08G 1/07* (2013.01); *G08G 1/093* (2013.01); *G08G 1/097* (2013.01); *G08G 1/0962* (2013.01); *G08G 1/0965* (2013.01); *G08G 1/0967* (2013.01); *G08G 1/096725* (2013.01); *G08G 1/096741* (2013.01); *G08G 1/096775* (2013.01); *G08G 1/096811* (2013.01); *G08G 1/096822* (2013.01); *G08G 1/096838* (2013.01); *H04B 1/3822* (2013.01); *H04B 7/18504* (2013.01); *H04L 9/3247* (2013.01); *H04L 67/02* (2013.01); *H04L 67/306* (2013.01); *H04M 15/60* (2013.01); *H04W 4/024* (2018.02); *H04W 4/029* (2018.02); *H04W 4/40* (2018.02); *H04W 4/42* (2018.02); *H04W 4/50* (2018.02); *H04W 12/08* (2013.01); *A61B 5/024* (2013.01); *A61B 5/0531* (2013.01); *B60W 2040/0809* (2013.01); *B60W 2040/0872* (2013.01); *B60W 2540/22* (2013.01); *B60W 2552/00* (2020.02); *B60W 2555/20* (2020.02); *B60W 2710/1044* (2013.01); *B60W 2710/18* (2013.01); *B60W 2720/10* (2013.01); *B64C 2201/123* (2013.01); *G01C 21/3608* (2013.01); *G06Q 50/30* (2013.01); *G06Q 2240/00* (2013.01); *H04W 4/48* (2018.02)

(58) Field of Classification Search
CPC ............ G02C 21/3667; G02C 21/3679; G02C 21/3685; H04W 4/046; G01C 21/3608; G06F 17/30864; G06F 17/30867; G06F 17/3087; G06F 17/30442; G06F 17/30477; G06F 17/30554; G06F 17/3053; G06F 17/025; G06F 17/026; G06F 17/027; G06F 17/028; G08G 1/096833
USPC .......................... 701/411, 424, 426, 465, 533
See application file for complete search history.

(56) References Cited

U.S. PATENT DOCUMENTS

| | | | | |
|---|---|---|---|---|
| 6,801,850 | B1* | 10/2004 | Wolfson | G01C 21/3415 340/995.23 |
| 6,895,329 | B1* | 5/2005 | Wolfson | G01C 21/3415 340/988 |
| 6,963,294 | B2* | 11/2005 | Kurosawa | G01C 21/3635 340/995.19 |
| 7,155,339 | B2* | 12/2006 | Tu | G01C 21/3679 701/426 |
| 7,822,546 | B2* | 10/2010 | Lee | G01C 21/3461 340/988 |
| 7,831,384 | B2* | 11/2010 | Bill | G01C 21/3407 340/995.14 |
| 7,952,494 | B2* | 5/2011 | Oota | G01C 21/365 340/995.1 |
| 8,185,380 | B2* | 5/2012 | Kameyama | G08G 1/0962 434/362 |
| 8,188,887 | B2* | 5/2012 | Catten | G08G 1/096716 340/905 |
| 8,397,171 | B2* | 3/2013 | Klassen | G01C 21/3682 345/157 |
| 8,417,449 | B1* | 4/2013 | Denise | G01C 21/36 701/411 |
| 8,433,512 | B1* | 4/2013 | Lopatenko | G01C 21/3679 701/400 |
| 8,458,177 | B2* | 6/2013 | Athsani | H04W 4/029 707/732 |
| 8,645,061 | B2* | 2/2014 | Newson | G01C 21/3484 701/117 |

(56) References Cited

U.S. PATENT DOCUMENTS

| | | | |
|---|---|---|---|
| 8,775,070 B1* | 7/2014 | Bhatia | G01C 21/3461 701/425 |
| 8,949,212 B1* | 2/2015 | Dhandapani | G06F 16/148 707/706 |
| 8,972,318 B2* | 3/2015 | Prakash | G06F 16/9535 706/45 |
| 9,303,997 B2* | 4/2016 | McGavran | G06N 5/04 |
| 9,767,209 B2* | 9/2017 | Stallman | G06F 16/9537 |
| 9,794,636 B2* | 10/2017 | Bayer | H04N 21/4826 |
| 9,921,070 B1* | 3/2018 | Nimchuk | G01C 21/343 |
| 9,959,339 B2* | 5/2018 | Ashton | G06F 16/322 |
| 10,140,785 B1* | 11/2018 | Cox | G07C 5/02 |
| 10,354,527 B2* | 7/2019 | DiMeo | G08G 1/0967 |
| 2003/0229441 A1* | 12/2003 | Pechatnikov | G01C 21/3679 701/411 |
| 2007/0010942 A1* | 1/2007 | Bill | G01C 21/3617 701/424 |
| 2008/0077318 A1* | 3/2008 | Saito | G06F 16/29 701/516 |
| 2008/0091347 A1* | 4/2008 | Tashiro | G01C 21/30 701/448 |
| 2008/0221787 A1* | 9/2008 | Vavrus | G01C 21/3469 701/423 |
| 2009/0005964 A1* | 1/2009 | Forstall | G01C 21/3492 701/533 |
| 2009/0012953 A1* | 1/2009 | Chu | H04W 4/029 |
| 2009/0093259 A1* | 4/2009 | Edge | H04W 4/06 455/456.3 |
| 2010/0036601 A1* | 2/2010 | Ozawa | G08G 1/096894 701/465 |
| 2010/0057351 A1* | 3/2010 | Woo | G01C 21/26 701/532 |
| 2010/0094543 A1* | 4/2010 | Friedenthal | G01C 21/343 701/533 |
| 2010/0121803 A1* | 5/2010 | Gill | G06Q 10/04 706/46 |
| 2010/0168994 A1* | 7/2010 | Bourque | G08G 1/096883 701/532 |
| 2010/0217517 A1* | 8/2010 | Oohashi | G01C 21/30 701/533 |
| 2010/0228473 A1* | 9/2010 | Ranford | G06Q 10/1095 701/465 |
| 2010/0248746 A1* | 9/2010 | Saavedra | G01C 21/3679 455/456.3 |
| 2010/0262449 A1* | 10/2010 | Monteforte | H04L 67/306 705/7.34 |
| 2010/0283432 A1* | 11/2010 | Ellwanger | B60K 35/00 320/155 |
| 2010/0305848 A1* | 12/2010 | Stallman | G06F 16/9537 701/465 |
| 2010/0332130 A1* | 12/2010 | Shimizu | G01C 21/3617 701/533 |
| 2011/0126146 A1* | 5/2011 | Samuelson | G06F 16/954 715/777 |
| 2011/0131243 A1* | 6/2011 | Aben | G01C 21/3611 707/771 |
| 2011/0153186 A1* | 6/2011 | Jakobson | G01C 21/20 701/532 |
| 2011/0202221 A1* | 8/2011 | Sobue | B60L 15/2045 701/22 |
| 2011/0301835 A1* | 12/2011 | Bongiorno | G06Q 10/02 705/6 |
| 2012/0158289 A1* | 6/2012 | Bernheim Brush | G06F 16/248 701/425 |
| 2013/0031208 A1* | 1/2013 | Linton | G09B 7/02 709/217 |
| 2013/0110633 A1* | 5/2013 | Waldman | G01C 21/20 705/14.58 |
| 2013/0166196 A1* | 6/2013 | Narasimha | G01C 21/3682 701/426 |
| 2013/0191020 A1* | 7/2013 | Emani | G01C 21/3492 701/468 |
| 2013/0217414 A1* | 8/2013 | Nagaraj | G01S 5/0257 455/456.2 |
| 2013/0219307 A1* | 8/2013 | Raber | G06F 8/38 715/763 |
| 2013/0238241 A1* | 9/2013 | Chelotti | G01C 21/362 701/533 |
| 2013/0288716 A1* | 10/2013 | Kwon | H04W 4/027 455/456.3 |
| 2013/0325780 A1 | 12/2013 | Prakash et al. | |
| 2014/0148970 A1* | 5/2014 | Dufford | G01C 21/3617 701/1 |
| 2014/0172294 A1* | 6/2014 | Kalra | G01C 21/3484 701/465 |
| 2014/0200804 A1* | 7/2014 | Wippler | G01C 21/3611 701/465 |
| 2014/0213300 A1* | 7/2014 | Spears | H04W 8/18 455/456.3 |
| 2014/0278070 A1* | 9/2014 | McGavran | G06N 20/00 701/465 |
| 2014/0309927 A1* | 10/2014 | Ricci | G01C 21/26 701/424 |
| 2014/0365120 A1* | 12/2014 | Vulcano | G01C 21/3617 701/532 |
| 2015/0106011 A1* | 4/2015 | Nesbitt | G01C 21/3679 701/412 |
| 2015/0120192 A1* | 4/2015 | Ron | G01C 21/3605 701/539 |
| 2015/0127210 A1* | 5/2015 | Suzuki | G01C 21/3664 701/29.1 |
| 2015/0228129 A1* | 8/2015 | Cox | G01S 19/13 701/29.1 |
| 2015/0233727 A1* | 8/2015 | Roelle | G01C 21/3697 701/533 |
| 2015/0275788 A1* | 10/2015 | Dufford | B60W 10/08 701/102 |
| 2016/0033290 A1* | 2/2016 | Inoue | G01C 21/3679 701/400 |
| 2016/0061617 A1* | 3/2016 | Duggan | G06F 16/248 701/538 |
| 2016/0123752 A1* | 5/2016 | Kandula | G01C 21/3469 701/123 |
| 2016/0147416 A1* | 5/2016 | Macfarlane | G01C 21/00 715/747 |
| 2016/0202074 A1* | 7/2016 | Woodard | G01C 21/34 701/465 |
| 2016/0202076 A1* | 7/2016 | Feng | G01C 21/343 701/408 |
| 2016/0226995 A1* | 8/2016 | Senarath | H04W 4/021 |
| 2016/0227464 A1* | 8/2016 | Senarath | G08G 1/096775 |
| 2016/0229402 A1* | 8/2016 | Morita | G08G 1/096758 |
| 2016/0349075 A1* | 12/2016 | Son | G01C 21/3697 |
| 2016/0360336 A1* | 12/2016 | Gross | H04M 1/72583 |
| 2017/0102244 A1* | 4/2017 | Meredith | G01C 21/3629 |
| 2017/0219373 A1* | 8/2017 | DiMeo | G01C 21/3415 |
| 2018/0037136 A1* | 2/2018 | Nelson | B60L 53/51 |
| 2018/0053121 A1* | 2/2018 | Gonzalez | G06Q 10/025 |
| 2018/0232641 A1* | 8/2018 | Bostick | G06N 5/04 |
| 2018/0236894 A1* | 8/2018 | Bandai | B60L 58/33 |
| 2019/0026852 A1* | 1/2019 | Senarath | G08G 1/096716 |

OTHER PUBLICATIONS

Corresponding International Patent Application No. PCT/US2015/018440, International Search Report and Written Opinion dated Jun. 18, 2015.

* cited by examiner

US 10,803,747 B2

PRESENTING GEOGRAPHIC SEARCH RESULTS USING LOCATION PROJECTION AND TIME WINDOWS

CROSS-REFERENCE TO RELATED APPLICATIONS

This application claims priority to and is a continuation of U.S. patent application Ser. No. 15/123,022, filed on Sep. 1, 2016 and titled "PRESENTING GEOGRAPHIC SEARCH RESULTS USING LOCATION PROJECTION AND TIME WINDOWS", which claims priority to U.S. Patent Application No. 61/946,962, filed on Mar. 3, 2014, which are incorporated herein by reference.

BACKGROUND

Within the field of computing, many scenarios involve devices that provide location-based search results to a user in transit in a vehicle. For example, a driver of an automobile may request information about locations that provide fuel, food, lodging, rest breaks, and vehicle maintenance. A device may compare the current location of the user with nearby locations to identify locations that may fulfill the location query. The identified locations may be sorted and/or filtered, e.g., by location type, the user's preferences, or other factors such as cost or popularity. The identified locations may be presented to the user as a set of query results, optionally including such information as distance, popularity rating, a link to a website with more information about the location (e.g., hours of operation and/or a restaurant menu), and/or an option to contact the location. A device may also enable the user to select a query result, and may adjust a route of the vehicle to include the selected location (e.g., an autonomously controlled vehicle may transition to a new route to visit the selected location, or a navigation device may adjust a map and a set of directions presented to the driver to include the selected location). In this manner, such devices may enable the user to perform location-based searches in the context of current transit in a vehicle.

In some cases, the user may specify details of the user's future plans in order to refine the location query. As a first such example, the user may specify a route between the current location of the vehicle and a destination, and may request a list of query results for locations that are near the route, along with information as to the added time of visiting the respective locations. As a second such example, the user may specify a target location farther along the route, e.g., a city where the user intends or prefers to stop, and may request a list of locations in the vicinity of the specified target location. In this manner, the user may refine the location query according to the user's plans for further transit in the vehicle.

SUMMARY

This Summary is provided to introduce a selection of concepts in a simplified form that are further described below in the Detailed Description. This Summary is not intended to identify key factors or essential features of the claimed subject matter, nor is it intended to be used to limit the scope of the claimed subject matter.

While the presentation of locations in response to a location query may be adaptable by the user to satisfy the user's future travel plans, in some circumstances, such information may not be available, or may be specified by the user in a different manner. As a first such example, the user may not have specified a route, either because the user is unwilling or has neglected to specify such a route; because the user has not yet decided on a route, or is considering alternative routes; or because the user is seeking information about the locations along alternative routes. As a second such example, the user may have an interest that is not urgent or immediate, but that is to be fulfilled in the future. In these cases, the user may adjust the location query and/or review the query results in view of the user's anticipated plans, but the search results may be poorly aligned with such unspecified information and/or anticipated plans. That is, the query results may include many locations that do not fit with the user's intent, and/or may exclude locations that closely align within the user's intent, but for which the device was unable to identify such close alignment and therefore excluded from the query results. As a result, the user may have to perform several queries with incremental refinements, defer the presentation of the query until a future time, and/or mentally compensate for the inaccurate alignment of the user's interests and the query results.

Presented herein are techniques for fulfilling a location query in a manner that may be able to compensate for unspecified and/or undecided information, and/or to choose the timing of the query according to the timing of the user's interests. For a particular query, a device may identify a timing window for query results of the location query to be presented to the user. The device may also monitor the transit of the vehicle to predict a route intended by the user, and predict a projected location of the vehicle along the route during the timing window. The device may use this information to identify at least one location that satisfies the location query, and that is also within a proximity range of the projected location. The device may therefore present the at least one location to the user as a query result of the location query in accordance with the techniques presented herein.

Another example of the techniques presented herein involves a server that fulfills location queries of users of vehicles in transit. The server comprises a processor, and a device communicator that communicates with a device within the vehicle. The server also comprises a memory storing instructions that, when executed by the processor, provide a system that fulfills location-based queries. The system comprises a query timing evaluator that identifies a timing window for query results of the location query to be presented to the user; a location projector that monitors the transit of the vehicle to predict a route intended by the user, and predicts a projected location of the vehicle along the route during the timing window; and a query result presenter that identifies at least one location that satisfies the location query and that is within a proximity range of the projected location, and presents the at least one location to the user as a set of query results of the location query, in accordance with the techniques presented herein.

Yet another example of the techniques presented herein involves a device that fulfills a location query of a user of a vehicle in transit. The device comprises a processor, and a location detector that detects a current location of the vehicle. The device also comprises a memory storing instructions that, when executed by the processor, provide a system that fulfills the location query. The system comprises a route predictor that monitors the current location in transit of the vehicle to predict a route intended by the user, and a query transmitter that transmit, to a location query provider, the route predicted for the transit of the vehicle, and a location query of the user of the vehicle. The system also comprise a query result presenter that, upon receiving from the location query provider at least one location identified as satisfying the location query and that is within a proximity range of the projected location and a timing window for query results of the location query to be presented to the user, present the at least one location to the user as a query result of the location query in accordance with the timing window, in accordance with the techniques presented herein.

To the accomplishment of the foregoing and related ends, the following description and annexed drawings set forth certain illustrative aspects and implementations. These are indicative of but a few of the various ways in which one or more aspects may be employed. Other aspects, advantages, and novel features of the disclosure will become apparent from the following detailed description when considered in conjunction with the annexed drawings.

DETAILED DESCRIPTION

Figure 1:
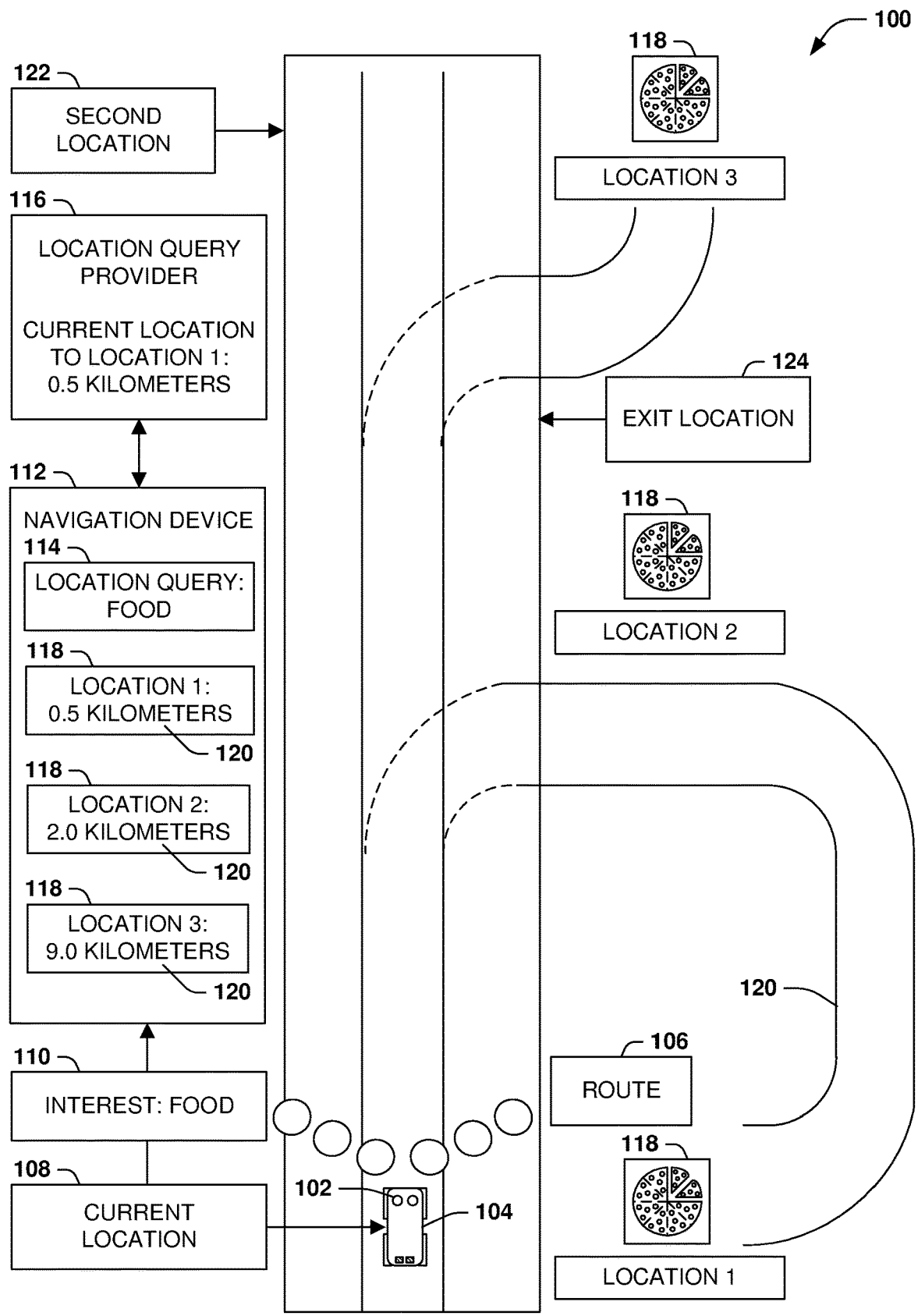
FIG. 1 is an illustration of an example scenario featuring a fulfillment of a location query submitted by a user within a vehicle in transit.

The claimed subject matter is now described with reference to the drawings, wherein like reference numerals are used to refer to like elements throughout. In the following description, for purposes of explanation, numerous specific details are set forth in order to provide a thorough understanding of the claimed subject matter. It may be evident, however, that the claimed subject matter may be practiced without these specific details. In other instances, structures and devices are shown in block diagram form in order to facilitate describing the claimed subject matter.

A. Introduction

FIG. 1 is an illustration of an example scenario 100 featuring a fulfillment of a location query 114 provided by a user 102 within a vehicle 104 in transit. In this example scenario 100, the user 102 may realize an interest 110, such as a desire to stop for food, lodging, a rest break, or refueling of the vehicle 102, and may formulate a location query 114 requesting information about the interest 110. For example, the user 102 may provide a set of keywords (e.g., "pizza restaurants") through text entry or voice command to a navigation device 112, which may in turn submit the location query 114 to a location query provider 116. Additionally, the navigation device 112 may detect or receive a current location 108 of the vehicle 104 (e.g., using a global positioning system (GPS) receiver), and may submit the current location 108 of the vehicle 104 to the location query provider 116 as a request for locations 118 that fulfill the location query 114 and that are also within the vicinity of the current location 108 of the vehicle 104. The location query provider 116 may review a database of locations 118 for those that satisfy the specified criteria, and may provide to the navigation device 112 a set of matching locations 118, optionally specifying such information as a distance of the location 118 from the current location 108; a popularity rating of the location 118; a link to a website with more information about the location (e.g., hours of operation and/or a restaurant menu); and/or an option to contact the location 118. The navigation device 112 may present such information to the user 102, optionally sorted and/or filtered by criteria such as distance, popularity, and/or user preference. Upon receiving from the user 102 a selection of a location 118, the navigation device 112 may present a map and/or route from the current location 108 to the selected location 118. Additionally, if the navigation device 112 is providing navigation assistance to the user 102 along a route 106, the navigation device 112 may add the location 118 to the route 106, and may update an estimated time of arrival at the terminal destination of the route 106 to account for the additional stop at the selected location 118. In this manner, the navigation device 112 and the location query provider 116 may interoperate to fulfill the location query 114 of the user 102.

Additional searching, sorting, and/or filtering may be performed in fulfillment of other information provided by the user 102. As a first such example, the user 102 may request query results for locations 118 that are nearby a second location, such as a distant city or the destination of the user 102, and the location query provider 116 may use the specified location instead of the current location 108 of the user 102. As a second such example, the user 102 may request query results for all locations 118 along a current route 106, such a list of restaurants that are available at each exit from a highway, and may choose to orient the route 106 and/or transit of the vehicle 104 after reviewing and selecting a location 118.

While the techniques presented in the example scenario 100 of FIG. 1 may be suitable for some such scenarios, other scenarios may present details or circumstances that limit the value of the identification and presentation of query results in this manner.

As a first such example, the navigation device 112 may perform distance evaluation by determining a straight-line distance from the current location 108 of the vehicle 104 to the respective locations 118 comprising the query results. However, in many circumstances, such information may be inaccurate. For example, a first location 118 of the result set may appear to be closer to the user 102, the vehicle 104, and/or the route 106 (e.g., adjacent to a highway), but the route 120 to the location 118 may involve an extensive detour that significantly adds to the length and/or duration of the route 106 of the user 102. Additionally, a second location 118 may appear to be within a reasonable distance of the user 102, but may not actually be accessible to the user 102, e.g., because no nearby exit from the highway where the user 102 is traveling connects to the location 118.

As a second such example, in some scenarios, the navigation device 112 may not be informed of a route of the user 102. This may arise, e.g., if the user 102 has neglected to specify a route 106; is unwilling to specify a route 106 (e.g., if the user 102 wishes to keep the route 106 private, or wishes to explore the options for a set of routes 106); and/or if the user 102 has not yet decided upon a route 106, but is driving without a destination in mind. As a result, the navigation device 112 may only be able to present query results for locations 118 that are in the vicinity of the current location 108 of the user 102, e.g., all locations 118 sorted in ascending order by distance from the current location 108, but may be unable to adjust the presentation of query results in any more sophisticated manner.

As a third such example, the user 102 may not wish to have an interest 110 fulfilled urgently or immediately, but, rather, may wish to submit a location query for locations within a timing window. For example, the user 102 may not be interested in stopping for food immediately, but, rather, may wish to stop for food in approximately 30 minutes. However, the navigation device 112 and/or location query provider 116 may not have any way of specifying the timing window of the location query 114, and the user 102 may have to perform additional steps in order to have such a location query 114 fulfilled.

As a fourth such example, the user 102 may attempt to predict a location where the user 102 may be in 30 minutes, and then submit the location query 114 specifying the selected location. However, burdening the user 102 with these additional steps may be problematic, e.g., if the user 102 does not know or cannot safely investigate a map to perform such prediction (e.g., while the user 102 is driving the vehicle 104), if the user 102 has not yet decided on a route 106, or if the user 102 wishes to review such options for alternative options for the transit of the vehicle 104.

As a fifth such example, the user 102 may select among the query results based on where the user 102 predicts to be during the timing window (e.g., predicting that the user 102 may wish to stop for food in 30 minutes, which may equate to 35 kilometers), and may therefore select from the query results a location 118 that is at approximately the indicated distance, but such projection by the user 102 may be inaccurate if the route 106 involves an extensive detour 120 or is inaccessible.

As a sixth such example, the user 102 may defer the submission of the location query 116 until within the timing window. However, the user 102 may forget about the location query 116 in the interim, or may unintentionally forego locations 118 due to routing complexities. For example, the user 102 may wait to submit the location query 116 until nearing a second location 122 where the user 102 wishes the location query 116 to be fulfilled. However, the user 102 may have already passed an exit location 124 for the location 118 that the user 102 preferred to select, and the user 102 may therefore have to backtrack to the exit location 124 and/or forego the preferred location 118. As yet another example, the location query 114 may provide an extensive set of query results, and the user 102 may have to choose a location 118 on an urgent basis upon nearing the second location 122, rather than evaluating the options in a relaxed manner while traveling between the current location 108 and the second location 122. These and other considerations may limit the value of fulfilling location queries of the user 102 in the manner illustrated in the example scenario 100 of FIG. 1.

B. Presented Techniques

Figure 2:
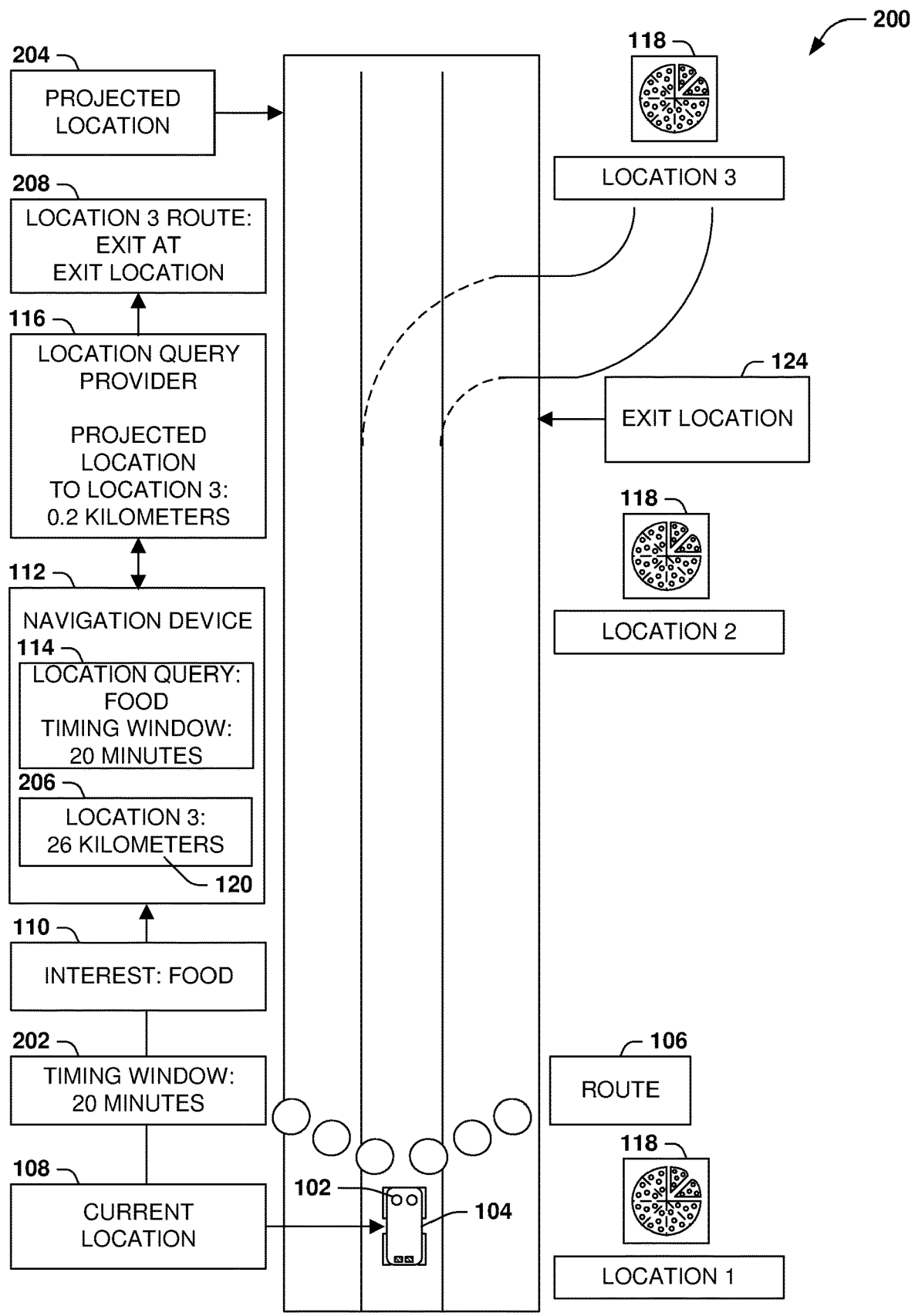
FIG. 2 is an illustration of an example scenario featuring a fulfillment of a location query submitted by a user within a vehicle in transit in accordance with the techniques presented herein.

FIG. 2 is an illustration of an example scenario 200 featuring techniques for fulfilling location query 116 of a user 102 in accordance with the techniques presented herein.

In this example scenario 200, the user 102 of the vehicle 104 submits a location query 114 specifying an interest 110, but also specifying a timing window 202, such as an interest in stopping for food in 20 minutes. The user 102 may specify this interest 110 and timing window 202 to the navigation device 112. Alternatively, the navigation device 112 may predict a timing window 202 for the location query 114 (e.g., based upon historic information indicating the user 102 typically stops for food every three hours, and is therefore likely to prefer the location query 114 to be fulfilled in 20 minutes). The navigation device 112 may also monitor the transit of the vehicle 104 to predict a route 106 intended by the user 102, e.g., based upon the user's likely destination, historic travel patterns, or popular choices among routes 106 from the current location 108. The navigation device 112 may therefore predict a projected location 204 of the vehicle 104 along the route 106 during the timing window 202, e.g., where the vehicle 104 is likely to be when the timing window 202 arrives. The navigation device 112 may the interact with the location query provider 116 to identify at least one location 118 that satisfies the location query 114, and also that is within a proximity range of the projected location 204. The navigation device 112 may therefore present, as the query results 206 of the location query 116, the locations 118 identified for the location query 114 and the timing window 202 to the user 102. Upon receiving a selection of a location 118 from the user 102, the navigation device 112 may perform a route adjustment of the route 106 to the selected location 208 in accordance with the selected location 118. For example, the navigation device 112 may store a reminder to exit at an exit location 124 before the projected location 204 in order to arrive at the selected location 118 near the projected location 204 and within the timing window 202 of the interest 110 of the user 102. In this manner, the navigation device 114 and the location query provider 116 may interoperate to fulfill the location query 114 of the user 102 in a manner that accounts for both a route 106 of the user 102 even if such a route 106 is not explicitly specified or definitely known, and that also accounts for the timing window 202 of the location query 116 with respect to the route 106, in accordance with the techniques presented herein.

C. Technical Effects

The techniques presented herein may provide a variety of technical effects in the scenarios provided herein.

As a first such example, the techniques provided herein may enable a fulfillment of a location query 114 of the user 102 in a manner that is more consistent with the intent of the user 102. For example, if the user 102 has to adjust the location query 114 to reflect the intent of the user 102 (e.g., having the user 102 identify the projected location 204 and/or specify a particular route 106), such adjustment may frustrate the user 102 if several refinements of the location query 114 are involved (e.g., the user 102 may have to submit multiple location queries 114 limited to different locations if several routes 106 are available). In some cases, the vehicle 104 may pass some opportunities for locations 118 while the user 102 is refining the location query 114. Such adjustment may also entail a safety risk, e.g., if the user 102 is also navigating the vehicle 104 while repeatedly adjusting the location query 114. The techniques presented herein enable an evaluation of the location query 116 that is more directly consistent of the intent of the user 102.

As a second such example, the techniques provided herein may assist with route planning, and/or may provide a more accurate assessment of the effect of a selected location 118 on the timing window 202. For example, if the user 102 is presented with query results reflecting the locations 118 that are suitable for the interest 110 of the user 102 during a future timing window 202, the user 102 may spend the intervening period considering the options before selecting a location 118 closer to the timing window 202 (e.g., the navigation device 112 may inform the user 102 that a first restaurant serving pizza and a second restaurant serving hamburgers are available near the projected location 204 within the timing window 202, and the user 102 may spend the intervening travel period deciding which restaurant is more appealing, and/or may defer the selection closer to the timing window 202). Accordingly, the presentation of query results according to a timing window 202 may inform the user 102 of the options that are projected to be available during the timing window 202 of the interest 110. Moreover, if the route planning involves an adjustment arising before the projected location 204 (e.g., an exit location 124 significantly before the projected location 204), the presentation of query results at the current location 108 may enable such adjustment, whereas presenting the query results closer to the projected location 204 and/or the timing window 202 may cause the user 102 to pass the exit location 124, who may then have to choose between backtracking to the exit location 124 and forego the preferred location 118.

As a third such example, the techniques provided herein may enable the navigation device 112 to assist with more comprehensive trip planning. For example, if the user 102 has a set of interests 110 that are to be fulfilled in different timing windows 202, the navigation device 112 may assist in the evaluation, comparison, and recommendation of schedules of locations 124 that may efficiently fulfill the interests 110 of the user 102 in accordance with the timing windows 202, e.g., consolidating timing windows 202 in order to reduce the number of stops at different locations 118. These and other technical effects may be achievable through the fulfillment of location queries 114 according to the projection of a projected location 204 within the timing window 202 and along a predicted route 106 of the user 102 during transit within the vehicle 104 in accordance with the techniques presented herein.

D. Example Embodiments

Figure 3:
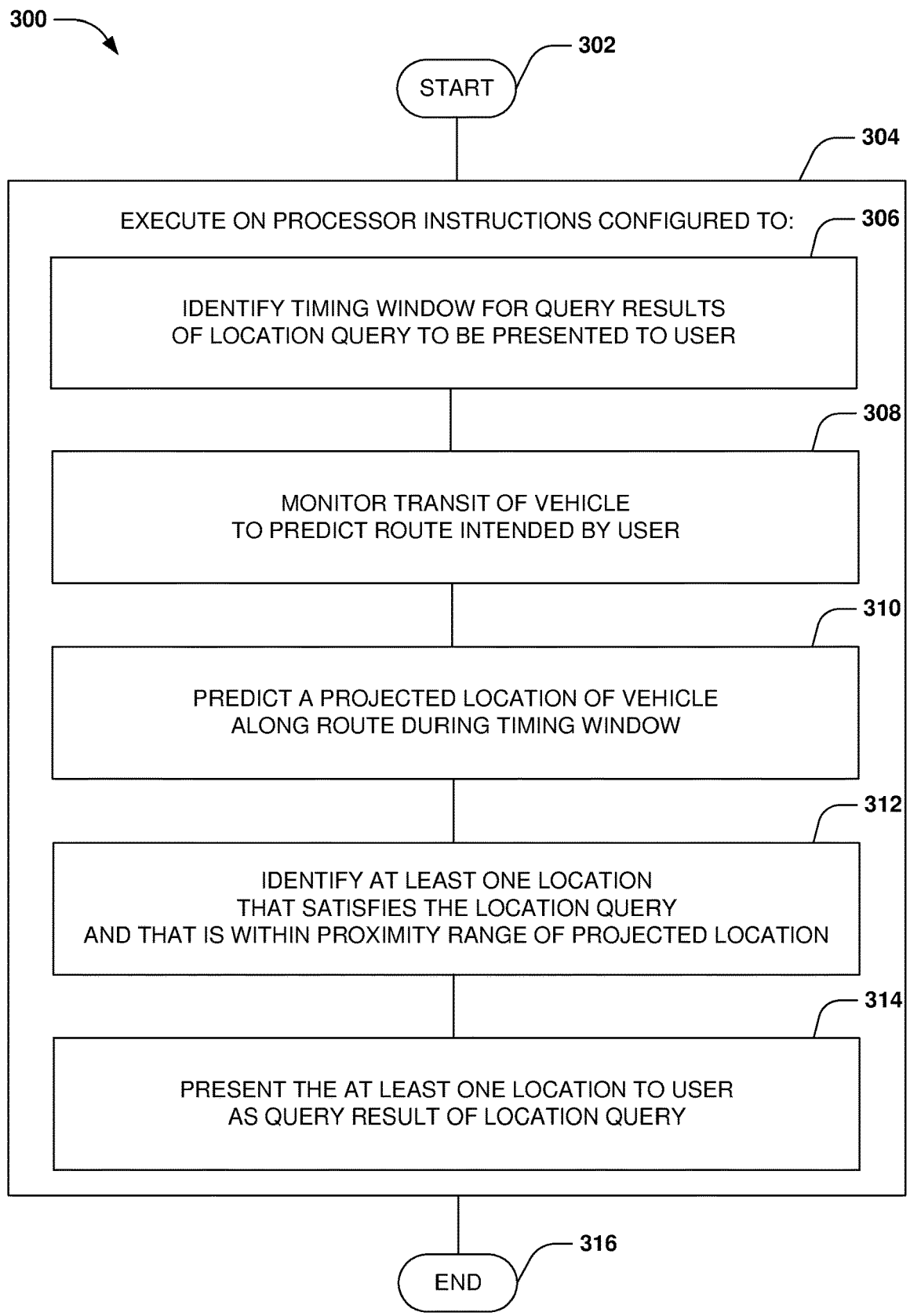
FIG. 3 is an illustration of an example method of a fulfillment of a location query submitted by a user within a vehicle in transit, in accordance with the techniques presented herein.

FIG. 3 presents a first example embodiment of the techniques presented herein, illustrated as an example method 300 of fulfilling a location query 114 of a user 102 in a vehicle 104 in transit. The example method 300 may be implemented on a device having a processor and a location detector that detects a current location 108 of the vehicle 104. The example method 300 may be implemented, e.g., as a set of instructions stored in a memory component of the device (e.g., a memory circuit, a platter of a hard disk drive, a solid-state memory component, or a magnetic or optical disc) that, when executed by the processor of the device, cause the device to perform the techniques presented herein.

The example method 300 begins at 302 and involves executing 304 the instructions on the processor. Specifically, the instructions cause the device to identify 306 a timing window 202 for query results of the location query 116 to be presented to the user 102. The instructions also cause the device to monitor 308 the transit of the vehicle 104 to predict a route 106 intended by the user 102. The instructions also cause the device to predict 310 a projected location 204 of the vehicle 104 along the route 106 during the timing window 202. The instructions also cause the device to identify 312 at least one location 118 that satisfies the location query 114 and that is within a proximity range of the projected location 204. The instructions also cause the device to present 314 the at least one location 118 to the user 102 as a query result of the location query 114. In this manner, the example method 300 enables the fulfillment of the location query 114 on behalf of the user 102 of the vehicle 104 in transit in accordance with the techniques presented herein, and so ends at 316.

Figure 4:
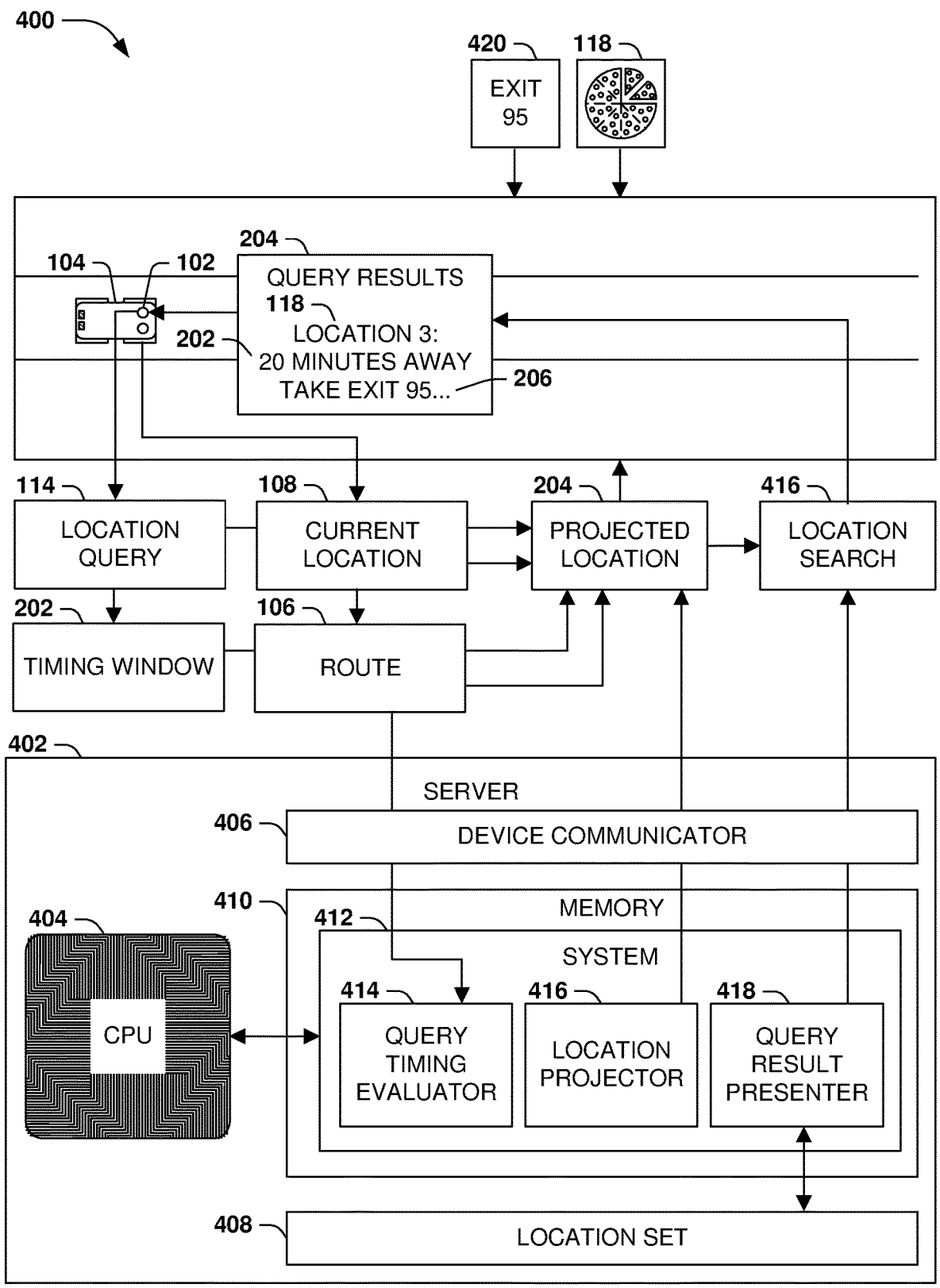
FIG. 4 is an illustration of a first example system for a fulfillment of a location query submitted by a user within a vehicle in transit, in accordance with the techniques presented herein.

FIG. 4 presents an illustration of an example scenario 400 featuring a second example embodiment of the techniques presented herein, illustrated as an example server 402 comprising a system 412 that fulfills a location query 114 of a user 102 of a vehicle 104 in transit. The example system 412 may be implemented, e.g., on a server 402 having a processor 404, a device communicator that communicates with a navigation device 112 within the vehicle 114, a location set 408 describing a set of locations 118, and a memory 408. A portion of the server 402 may be located on a navigation device 112 within the vehicle 104 of the user 102, and/or may be located at a remote location. Respective components of the example system 412 may be implemented, e.g., as a set of instructions stored in a memory 408 of the server 402 and executable on the processor 404 of the server 402, such that the interoperation of the components causes the server 402 to operate according to the techniques presented herein.

The example system 412 comprises a query timing evaluator 414, which identifies a timing window 202 for query results of the location query 114 to be presented to the user 102. The example system 412 also comprises a location projector 416, which monitors the transit of the vehicle 104 to predict a route 106 intended by the user 102, and predicts a projected location 204 of the vehicle 104 along the route 106 during the timing window 202. The example system 412 also comprises a query result presenter 418, which utilizes the location set 408 to identify at least one location 118 that satisfies the location query 114 and that is within a proximity range of the projected location 204, and presents the at least one location 118 to the user 102 as a set of query results of the location query 114, such as an exit ramp 420 that the user 102 is to take to arrive at the location 118. In this manner, the interoperation of the components of the example system 412 enables the server 402 to participate in the fulfillment of the location query 114 of the user 102 in the vehicle 104 in transit in accordance with the techniques presented herein.

Figure 5:
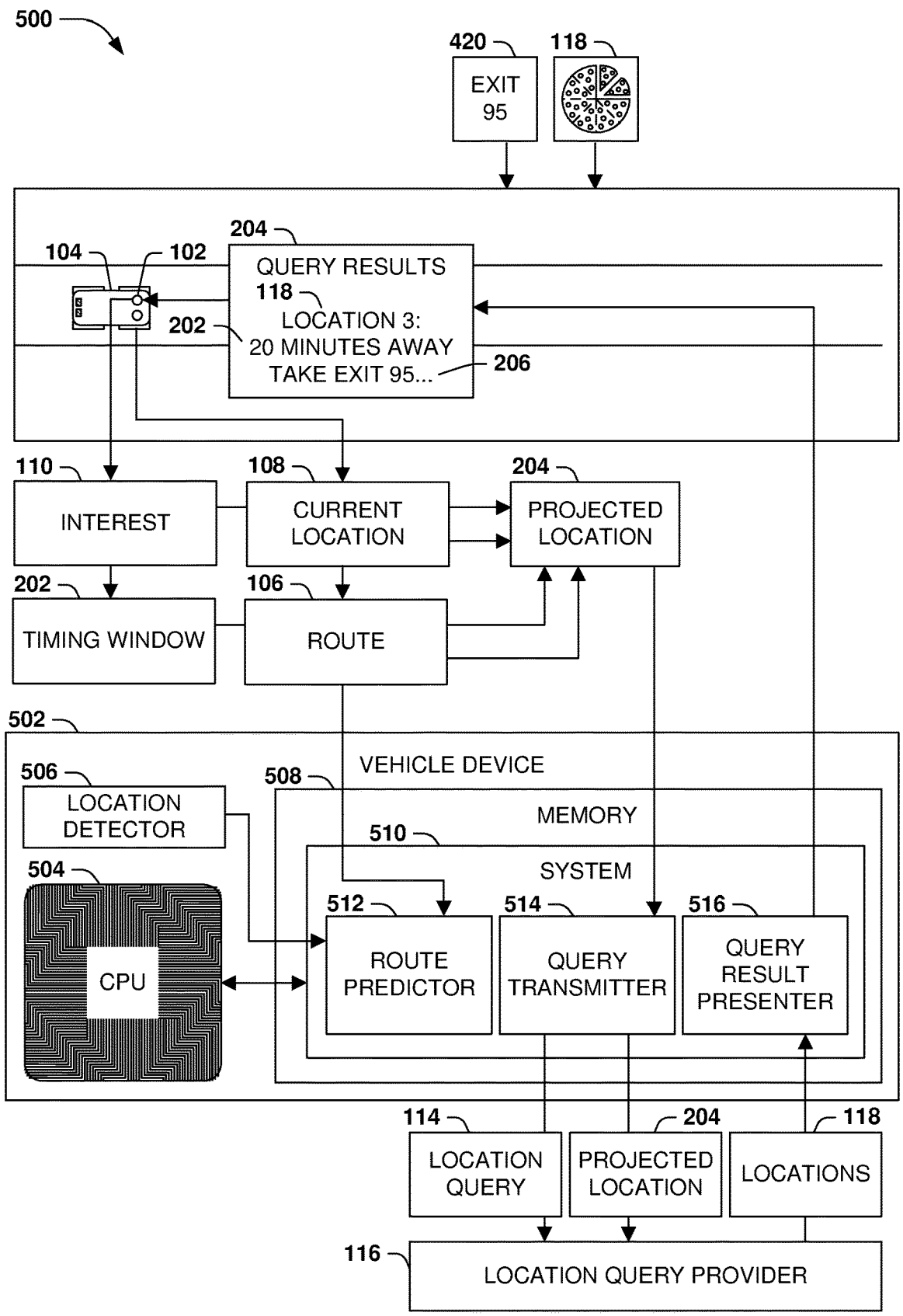
FIG. 5 is an illustration of a second example system for a fulfillment of a location query submitted by a user within a vehicle in transit, in accordance with the techniques presented herein.

FIG. 5 presents an illustration of an example scenario 500 featuring a third example embodiment of the techniques presented herein, illustrated as an example vehicle device 502 featuring an example system 510 that participates in the fulfillment of a location query 114 of a user 102 in the vehicle 104. The example system 510 may be implemented, e.g., on a vehicle device 502 having a processor 504; a location detector 506 that detects a current location 108 of the vehicle 104 (e.g., a global positioning system (GPS) coordinate); and a memory 508. Respective components of the example system 510 may be implemented, e.g., as a set of instructions stored in the memory 508 of the vehicle device 502 and executable on the processor 504 of the vehicle device 502, such that the interoperation of the components causes the vehicle device 502 to operate according to the techniques presented herein. The vehicle device 502 is also in communication with a location query provider 116, which may be remotely accessible to the vehicle device 502 and/or partly or wholly incorporated within the device 502, in order to fulfill a location query 114 according to a projected location 204.

The example system 510 comprises a route predictor 512, which monitors the current location 108 of the vehicle 104 in transit to predict a route 106 intended by the user 102. The example system 510 also comprises a query transmitter 514, which transmits, to the location query provider 116, the route 106 predicted for the transit of the vehicle 114, and an interest 110 of the user 102 of the vehicle 104 that may be expressed as a location query 114. The example system 510 also comprises a query result presenter 516, which, upon receiving from the location query provider 116 at least one location 118 identified as satisfying the location query 114 and that is within a proximity range of the projected location 204 and a timing window 202 for query results of the location query 114 to be presented to the user 102, presents the at least one location 118 to the user 102 as a query result of the location query 114. In this manner, the interoperation of the components of the example system 510 enables the vehicle device 502 to participate in the fulfillment of the location query 114 in accordance with the techniques presented herein.

Still another embodiment involves a computer-readable medium comprising processor-executable instructions configured to apply the techniques presented herein. Such computer-readable media may include, e.g., computer-readable storage media involving a tangible device, such as a memory semiconductor (e.g., a semiconductor utilizing static random access memory (SRAM), dynamic random access memory (DRAM), and/or synchronous dynamic random access memory (SDRAM) technologies), a platter of a hard disk drive, a flash memory device, or a magnetic or optical disc (such as a CD-R, DVD-R, or floppy disc), encoding a set of computer-readable instructions that, when executed by a processor of a device, cause the device to implement the techniques presented herein. Such computer-readable media may also include (as a class of technologies that are distinct from computer-readable storage media) various types of communications media, such as a signal that may be propagated through various physical phenomena (e.g., an electromagnetic signal, a sound wave signal, or an optical signal) and in various wired scenarios (e.g., via an Ethernet or fiber optic cable) and/or wireless scenarios (e.g., a wireless local area network (WLAN) such as WiFi, a personal area network (PAN) such as Bluetooth, or a cellular or radio network), and which encodes a set of computer-readable instructions that, when executed by a processor of a device, cause the device to implement the techniques presented herein.

Figure 6:
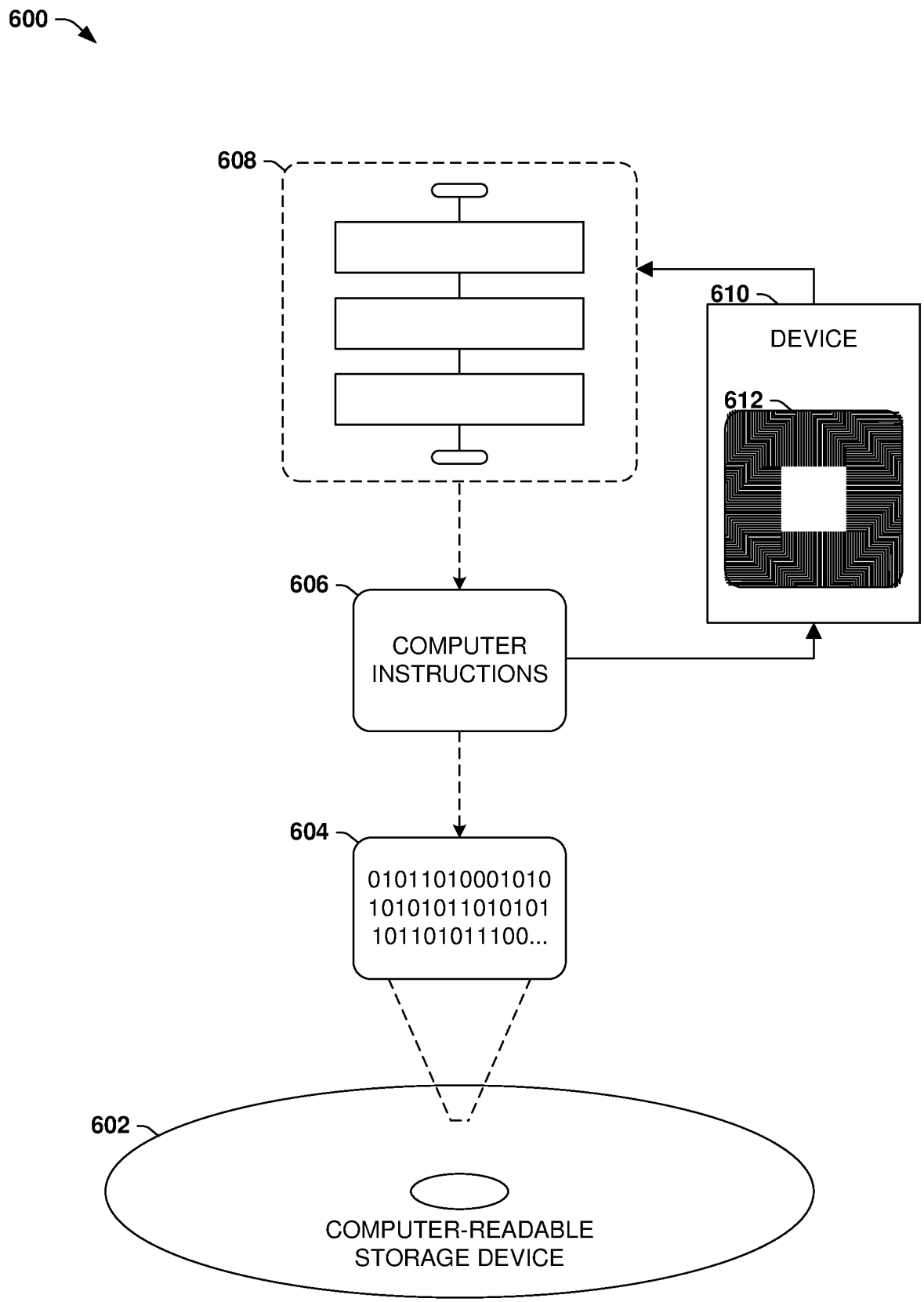
FIG. 6 is an illustration of an example computer-readable medium comprising processor-executable instructions configured to embody one or more of the provisions set forth herein.

An example computer-readable medium that may be devised in these ways is illustrated in FIG. 6, wherein the implementation 600 comprises a computer-readable medium 602 (e.g., a CD-R, DVD-R, or a platter of a hard disk drive), on which is encoded computer-readable data 604. This computer-readable data 604 in turn comprises a set of computer instructions 606 configured to operate according to the principles set forth herein. As a first such example, the computer instructions 606 may cause the device 610 to utilize a method of fulfilling a location query 114 of a user 102 of a vehicle 104 in transit, such as the example method 300 of FIG. 3. As a second such example, the computer instructions 606 may provide a system for fulfilling a location query 114 of a user 102 of a vehicle 104 in transit, such as the example system 412 in the example scenario 400 of FIG. 4, and/or the example system 510 of FIG. 5. Many such computer-readable media may be devised by those of ordinary skill in the art that are configured to operate in accordance with the techniques presented herein.

E. Variable Aspects

The techniques discussed herein may be devised with variations in many aspects, and some variations may present additional advantages and/or reduce disadvantages with respect to other variations of these and other techniques. Moreover, some variations may be implemented in combination, and some combinations may feature additional advantages and/or reduced disadvantages through synergistic cooperation. The variations may be incorporated in various embodiments (e.g., the example method 300 of FIG. 3; the example system 412 of FIG. 4; the example system 510 of FIG. 5; and the example computer-readable storage device 602 of FIG. 6) to confer individual and/or synergistic advantages upon such embodiments.

E1. Scenarios

A first aspect that may vary among embodiments of these techniques relates to the scenarios wherein such techniques may be utilized.

As a first variation of this first aspect, the techniques presented herein may be used with many types of vehicles 104, including automobiles, motorcycles, trucks, trains, buses, watercraft, aircraft, drones, and spacecraft. The techniques may also be utilized to fulfill the location queries 116 of the user 102 during transit of the vehicle 104 in many environments, such as a roadway, highway, sidewalk, dirt or grass path, waterway, and airspace. Such vehicles may be controlled by one or more humans, may be autonomous, or may involve a combination thereof, such as an autonomous automobile that can also be controlled by a human.

As a second variation of this first aspect, the techniques provided herein may be used to fulfill many types of location queries 114 involving many types of interests 110 of the user 102, and/or many types of locations 118. As a first such example, the interests 110 of the location query 114 may comprise personal interests of the user 102 and/or other individuals within or outside the vehicle 104, such as interests in food, rest breaks, lodging, network connectivity, entertainment, and shopping. As a second such example, the interests 110 of the location query 114 may comprise interests that relate to the vehicle 104, such as refueling, maintenance such as oil or windshield wiper fluid refills, and/or preventive or remedial maintenance such as a tire change or tire pressure check.

As a third variation of this first aspect, the timing window 202 for fulfilling the interest 110 may be specified in a variety of ways. As a first such example, the timing window 202 may be specified and/or determined in absolute terms (e.g., "at noon"), and/or in relative terms (e.g., "20 minutes from now"). Many such variations may be included in embodiments of the techniques presented herein.

E2. Route Prediction

A second aspect that may vary among embodiments of the techniques presented herein involves the manner of predicting the route 106 of the user 102.

Figure 7:
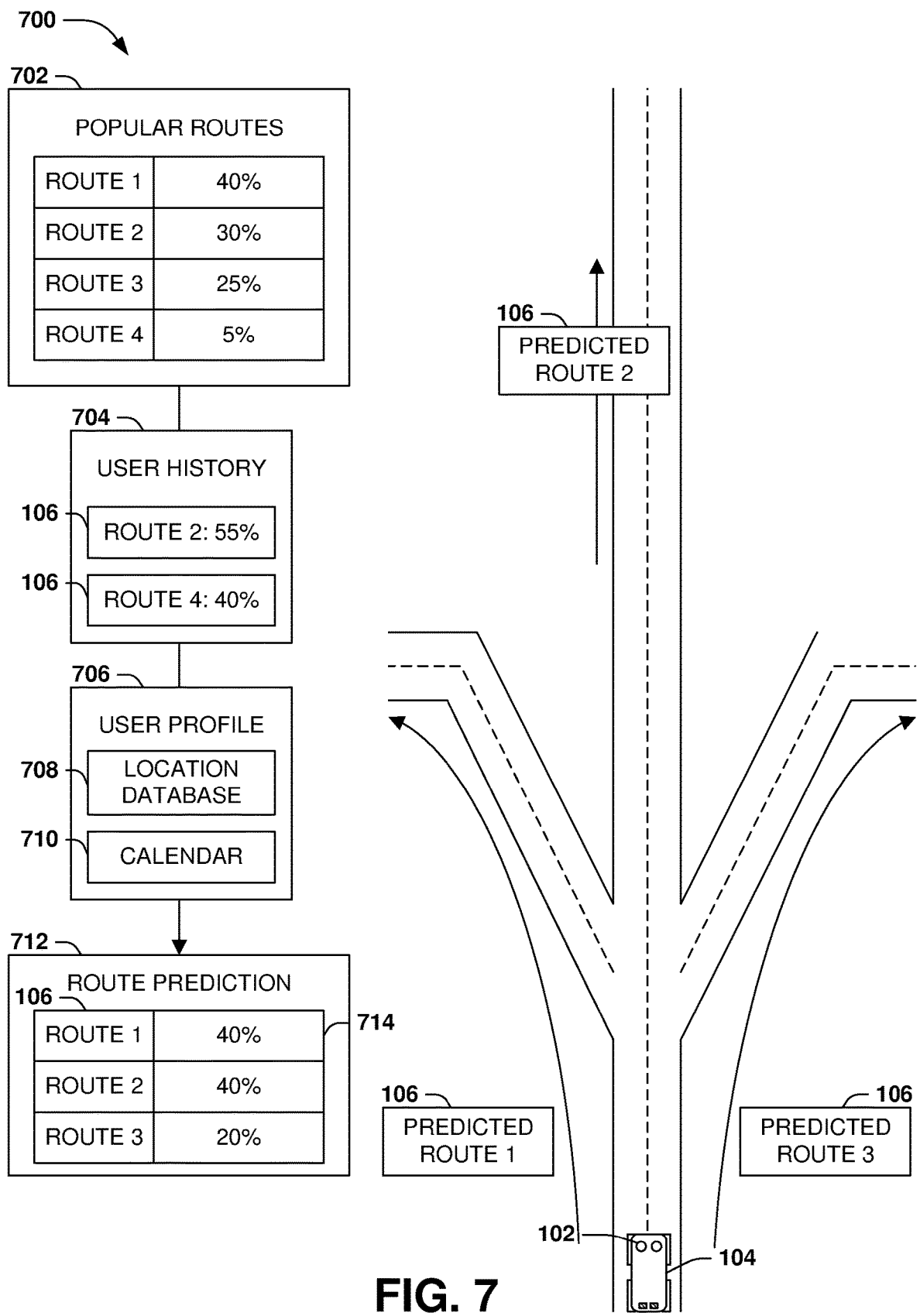
FIG. 7 is an illustration of an example technique for predicting a route of a user within a vehicle in transit, in accordance with the techniques presented herein.

FIG. 7 presents an illustration of an example scenario 700 featuring several techniques for predicting the route 106 of the user 102. In this exemplary scenario 700, the user 102 is navigating a vehicle 104 in transit along a road that branches in different directions, such that the user 102 may feasibly be following one of several routes 106. In order to determine which route 106 the user 102 intends to navigate, a device may utilize a variety of techniques. As a first such example, the device may have access to a historical route set of routes 106 that have previously completed by various users 102 of vehicles 104, such as a list of popular routes 702 of users 102 traveling through the current location 108 of the vehicle 104. The historical route set may indicate, e.g., the percentage of users 102 who have traveled through the current location 108 and then followed the respective routes 106. The device may therefore compare the transit of the vehicle 104 with the historical route set of routes 106 previously completed by users 102 to determine the likelihood that the user 102 intends to follow the route 106.

As a second variation of this second aspect, a device may have access to a user history 704 that specifies the routes 106 that the user 102 has previously taken while navigating the vehicle 104. The user history 704 may inform the route prediction, e.g., by comparing the similarity of the current transit of the vehicle 104 with other routes 106 that the user 102 has previously completed, such that even if the current transit varies (e.g., including a detour as compared with the previous route 106), the similarity of the previously traveled route 106 and the current transit of the vehicle 104 may inform the probability that the user 102 intends to complete a similar route 106 as previously traveled.

As a third variation of this second aspect, a device may have access to a user profile of the user 102 providing various personal information that may inform the prediction of the route 106 intended by the user 102. As a first such example, the user profile 706 may include a location database 708 of locations 118 that are known to the user 102, such as the residences of friends and family members, and the addresses of businesses that the user 102 patronizes. Transit in the direction of such a location 118 may indicate the intent of the user 102 to complete a particular route 106. As a second such example, the user profile 706 may include a calendar 710 indicating an upcoming event at a particular location 118 to which the user 102 is traveling, such as an appointment at a location 118 or travel to a distant city. Transit in the direction of the location 118 of such an event may inform the route prediction of the route 106 intended by the user 102.

These and other sources of information may inform a route prediction 716, which may result in a set of predicted routes 106 to various locations 118 and respectively having an intent probability 714 reflecting the probability that the user 102 intends to follow the route 106. A device may utilize such route predictions 712 in the application of the techniques presented herein. For example, for the respective predicted routes 106, the device may identify one or more locations 118 that are within a range of a projected location 204 along the predicted route 106. The device may present a set of such locations 118; e.g., after identifying a route set of at least two routes 106 respectively associated with an intent probability 714 that the user 102 intends to complete the route 106, and may sort the locations 118 according to the intent probabilities of the respective routes 106. Many techniques may be utilized to predict and utilize the route 106 intended by the user 102 during the transit of the vehicle 104 in accordance with the techniques presented herein.

E3. Timing Window Identification

A third aspect that may vary among embodiments of the techniques presented herein involves the manner of identifying the timing window 202 of the interest 110 of the user 102 in order to identify locations 118 near the projected location 204 along the predicted route 106 during the timing window 202.

As a first variation of this third aspect, a device may identify the timing window 202 of the location query 116 by identifying, in the location query 116 submitted by the user 102, a user-specified timing window 202. For example, the user 102 may simply specify the timing window 202 in which the user 102 wishes to visit a location 116 according to the interest 110 of the user 102, and the device may search for locations 118 that match the timing window 202 specified by the user 102.

As a second variation of this third aspect, a device may determine the timing window 202 for an interest 110 of the user 102 according to an operating metric of the vehicle 104, such as a metric of a fuel level, a vehicle maintenance schedule, or a driving behavior of the user 102 while operating the vehicle 104, such as the vehicle direction, speed, and/or acceleration. For example, the device may evaluate the operating metrics of the vehicle 104 (e.g., telemetry received from the vehicle 104 indicating its status and/or operation by the user 102), may identify a timing window 202 for refueling the vehicle 104 (e.g., refueling and/or recharging may be needed between 20 and 40 minutes from a present time), and may search for locations 118 of the user 102 that may be fulfilled at a projected location 204 along the route 106 that is within the timing window 202 determined by the operating metric of the vehicle 104.

As a third variation of this third aspect, a device may identify the timing window 202 for the location query 116 by identifying a set of transit contingencies of the transit of the vehicle 104 (e.g., the frequency with which the user 102 wishes to stop for food, lodging, or rest; the times of day when the user 102 prefers to travel; and the frequency with which two users 102 within a vehicle 104 trade the roles of driver and passenger). A device may monitor a status of the respective transit contingencies (e.g., comparing the typical duration with which a user 102 drives before a break with the duration since the user 102 last took a break), and may identify the timing window 202 of a location query 116 that reflects the status of the transit contingency. For example, the user 102 may initiate a location query 116 for rest stops, and the device may identify the typical length for which the user 102 typically continues to drive from the current location 108, and may then identify locations 118 that are near the projected location 204 along the predicted route 106 according to when the user 102 is anticipated to want to take a driving break. Such travel contingencies may recite both positive constraints on the selection of the timing window 202 (e.g., a desire to stop for a rest break 110 at least every two hours), and/or a negative constraint on the selection of the timing window 202 (e.g., a desire not to stop for a rest break more frequently than once every two hours, or not during a particular duration in which the user 102 is listening to a chapter of an audiobook). Moreover, a device may identify such transit contingencies in a variety of ways. For example, the user 102 may specify the transit contingencies (e.g., the user 102 may request stops for a driving break approximately every two hours along a route 106), and/or may monitor the transit of the vehicle 104 over time to detect the transit contingencies that the user 102 fulfills during routine transit of the vehicle 104, and store the transit contingencies detected during such transit of the vehicle 104 in the set of transit contingencies, for use in later identifying the timing window 202 of a location query 202.

Figure 8:
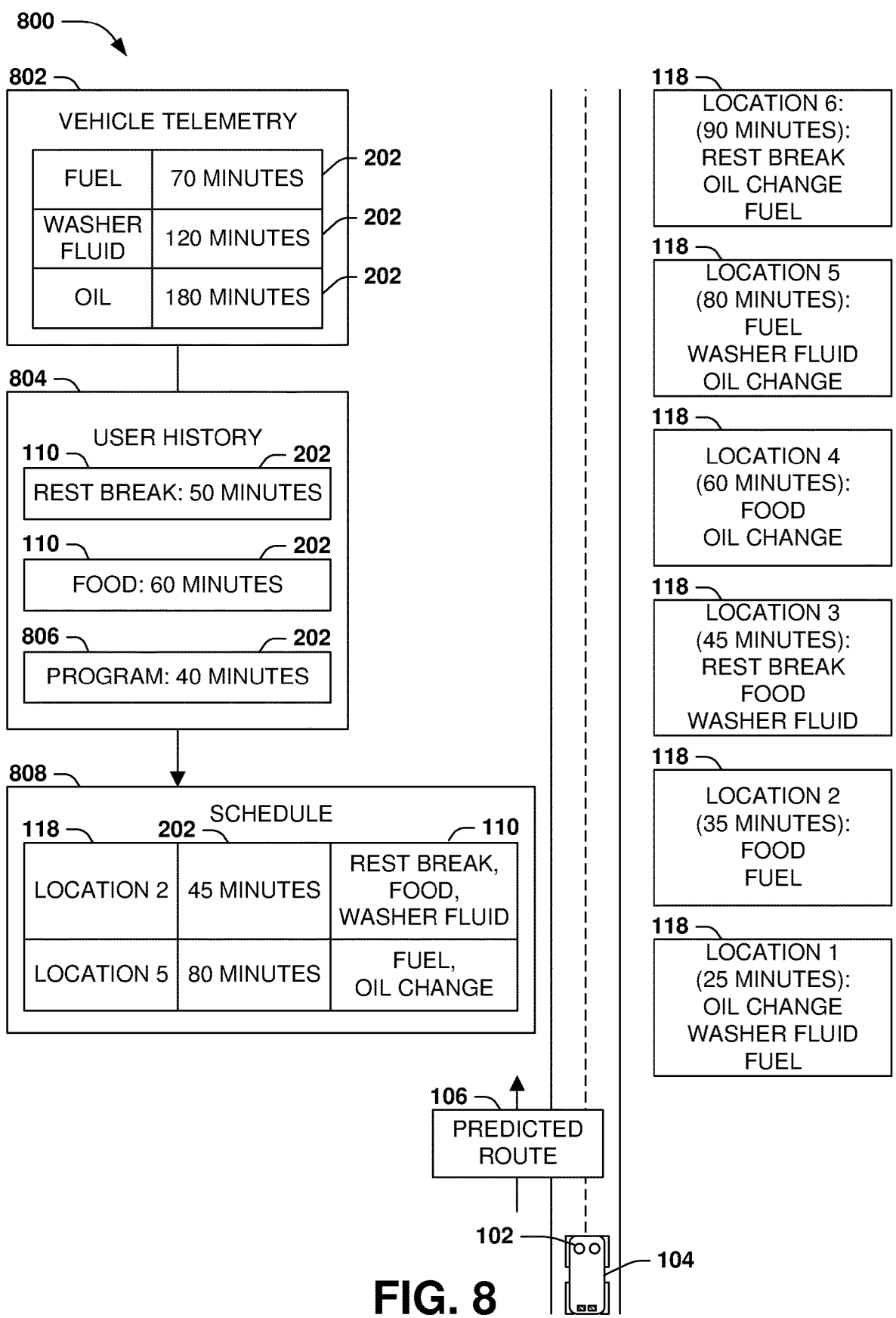
FIG. 8 is an illustration of an example technique for predicting the interests of a user and suggesting a schedule based on location queries, in accordance with the techniques presented herein.

FIG. 8 presents an illustration of an example scenario 800 featuring these and further variations of this third aspect, wherein a user 102 navigates a vehicle 104 along a predicted route 106. A device may identify a set of interests 110 of the user 102 that inform the selection of locations 118 and the timing windows 202 in which such interests 110 are to be fulfilled as a location query 114. As a first such example, the interests 110 of the user 102 may include properties of the vehicle 104, which may be detected according to vehicle telemetry 802 (e.g., maintenance stops for refueling, refilling a fluid level such as windshield washer fluid, and an oil check or change). As a second such example, the interests 110 of the user 102 may include personal interests (e.g., rest breaks and food), which may be determined via an evaluation of a user history 804, as well as the timing window 202 of the travel contingencies. Such interests 110 may also include a negative travel contingency, such as an indication that the user 102 is currently listening to an audio program that is estimated to last for another 40 minutes, and that the user 102 prefers not to interrupt such a program in order to visit a location 118. Moreover, the device may detect a number of locations 118 along the predicted route 106 where such interests 110 may be satisfied in accordance with the timing window 202 of such interests 110. The device may evaluate the locations 118 together with the interests 110 of the user 102 and the timing windows 110 thereof (e.g., using a best-fit algorithm), and may prepare and propose a schedule 808 of locations 118 to be visited along the route 118 that fulfill the interests 110 of the user 102 during the respective timing windows 202. Such evaluation may result in an optimization of the route 106 of the user 102. Moreover, the interests 110 may be prioritized; e.g., the timing window 202 for replenishing windshield washer fluid may be comparatively flexible, while the timing window 202 for refueling the vehicle 104 may construed strictly. Such prioritization may enable an optimization of the predicted route (e.g., if replenishing windshield washer fluid during the typical timing window 202 would entail an additional stop, the schedule 808 may reflect an earlier replenishing of the windshield washer fluid at a closer location 118 that reduces the number of stops along the predicted route 106). The prepared schedule 808 may be presented to the user 102, who may adjust the schedule 808 such as by adding, removing, or reordering interests 110 and timing windows 202. When the user 102 accepts the schedule 808, the device may assist the navigation of the vehicle 104 according to the schedule 808 in order to fulfill the respective interests 110 of the user 102 in accordance with the timing window 202 of each such interest 110 in accordance with the techniques presented herein.

Figure 9:
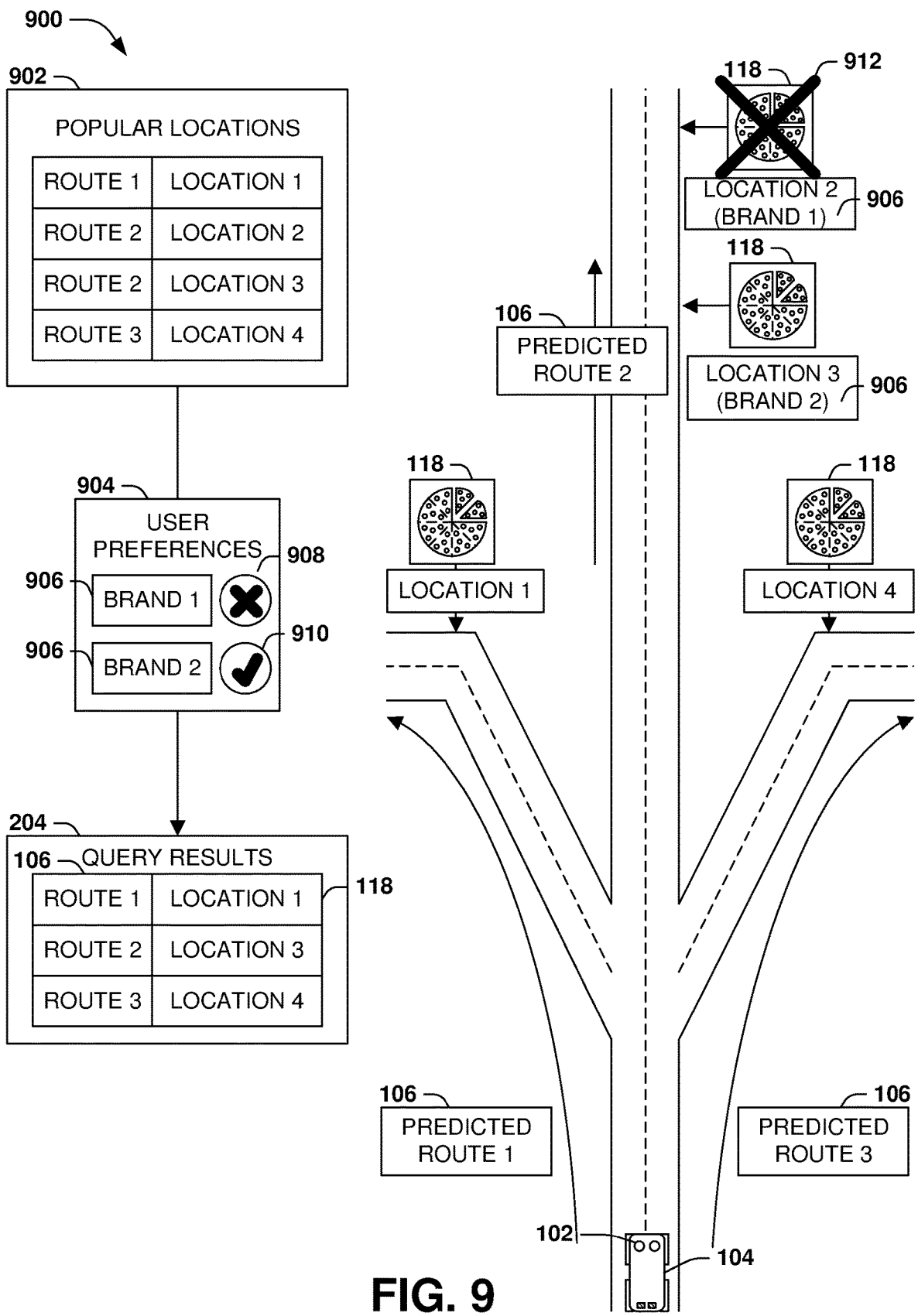
FIG. 9 is an illustration of an example technique for presenting query results for multiple predicted routes, in accordance with the techniques presented herein.

FIG. 9 presents an illustration of an exemplary scenario 900 featuring further variations of this third aspect, involving an adjustment of the selection of locations 118 for the location query 114. In this example scenario 800, a user 102 is navigating a vehicle 104 in a manner that may diverge into each of several predicted routes 106, and may initiate a location query 114 for an interest 110 such as food, as well as a timing window 202 for the interest 110. A navigation device 112 may predict both a first route 106 of the transit of the vehicle 104 and a second route 106 of the transit of the vehicle 104, and may present concurrently to the user 102 a first location 118 as a query result of the location query 114 for the first route 106, and a second location 118 as a query result of the location query 114 for the second route 106. For example, the navigation device 104 may first identify the projected location 204 along each predicted route 106, and identifying locations 118 that fulfill the location query 114 within the timing window 202 along each predicted route 106. Additionally, the presentation of locations 118 as search results for the location query 114 may be adapted, e.g., according to a set of user preferences 904 of the user 102, such as a dislike 908 of a first brand 906 that causes an exclusion 912 of a location 118 from the query results set, and an approval 910 of a second brand 906 that causes such locations 118 to be preferentially presented to the user 102, e.g., by sorting the set of query results according to the user preferences 904. As a second such example, the device may preferentially select locations 118 according to a user popularity among users 102 who have traveled along each predicted route 106 (e.g., either a generally high user popularity of the brand 906 as compared with other brands 906, or a particular user popularity for the particular predicted route 106, such as the best place for food along the predicted route 106). The navigation device 112 may therefore preferentially sort the top-rated restaurants within the travel window 202 along each predicted route 106. As a third such example, the navigation device 112 may filter the query results according to various factors; e.g., the respective locations 118 may be associated with an operating time window within which the location 118 is accessible and operating, and the navigation device 112 may remove, from the set of query results, locations 118 that are associated with an operating time window that does not overlap the timing window 202 of the location query 116 (e.g., locations 108 that are not accessible during the timing window 202). Accordingly, the navigation device 112 may present to the user 102 a set of locations 906 that satisfy the location query 116 and the timing window 202 along each predicted route 106. These and other techniques may be utilized to identify and utilize the timing window 202 in the selection of locations 118 as query results 206 of the location query 114 in accordance with the techniques presented herein.

E4. Presentation of Query Results and Location Selection

A fourth aspect that may vary among embodiments of these techniques relates to the manner of presenting query results 206 to the user 102, and of responding to the selection of a location 108 by the user 102.

Figure 10:
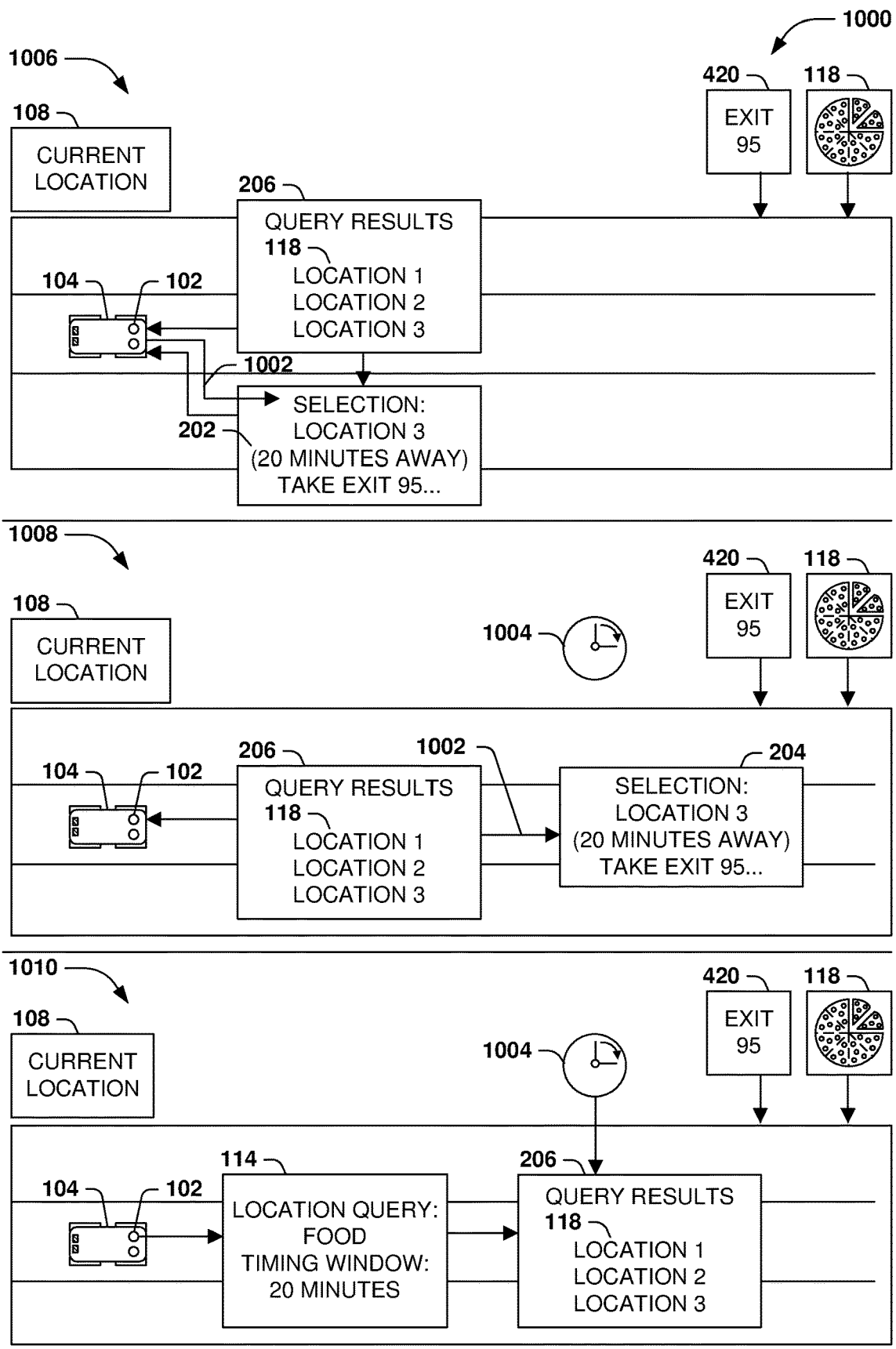
FIG. 10 is an illustration of an example technique for fulfilling a location query of a user in view of a timing window, in accordance with the techniques presented herein.

FIG. 10 presents an illustration of further variations of this fourth aspect, involving alternatives in the timing of the presentation of the query results 206 of a location query 114 to the user 102. In each example of this example scenario 1000, at a current location 108 of the vehicle 104, the user 102 initiates a location query 114 for which a timing window 202 is determined (e.g., a request for a location 118 for food in approximately 20 minutes). In a first such example 1006, a navigation device 112 of the vehicle 104 may promptly present a set of query results 206 for locations 118 for food that are within the timing window 202 along the route 106, and, upon receiving a selection 1002 of a location 118 from the user 102, may promptly update the route 106 of the transit of the vehicle 104 to reflect the selected location 118 (e.g., informing the user 102 promptly of a route adjustment, such as an exit ramp 410 that the user 102 is to take to arrive at the location 118. As a second example 1008, the navigation device 112 may receive the location query 114 at the current location 108 and may promptly present to the user 104 a set of query results 206 identifying the locations 118 along the predicted route 106 that are within the timing window 202 and that satisfy the location query 114. However, the user 102 may wait 1004 until the timing window 202 to provide a selection 1002 of a location 118, and the navigation device 112 may then update the route 106 of the transit of the vehicle 104 and present the route adjustment, such as directing the user 102 to take an exit ramp 420 in order to arrive at the location 108. The navigation device 112 may also present reminders to the user 102 closer to the timing window 202 if the user 102 has not yet initiated a selection 1002 of a location 118. As a third such example 1010, the user 102 may initiate the location query 14 at the current location 108, and the navigation device 112 may respond simply by storing the location query 114 for fulfillment closer to the timing window 202. Accordingly, after waiting 1004 for the timing window 202 to arrive, the navigation device 104 may present the query results 206 to the user 102, and may provide a route adjustment upon receiving a selection 1002 from the user 102. In this manner, the navigation device 112 may utilize the timing window 202 in various ways to present the query results 206 to the user 102 in accordance with the techniques presented herein.

As a second variation of this fourth aspect, a navigation device 112 may identify the query results 206 in a variety of ways. As one such example, upon receiving from the user 102 a location query 114 to be periodically updated during the transit of the vehicle 104, the navigation device 112 may store the location query 114, and may periodically update the at least one location 118 identified within the proximity range of the projected location 204 of the vehicle 104 that is within the timing window 202 along the route 102. For example, the user 102 may drive the vehicle 104 at a variable speed, such that the projected location 204 during the timing window 202 may change (e.g., the projected location 204 may be closer to the current location 108 where the location query 114 is initiated if the user 102 drives slow, and farther from the current location 108 where the location query 114 is initiated if the user 102 drives fast). The navigation device 112 may periodically update the query results to indicate the locations 118 within the timing window 202 as the projected location 204 changes.

As a third variation of this fourth aspect, a navigation device 112 may evaluate the query results 206 in view of the route adjustments that are involved in arriving at the locations 118 along the predicted route 106. For example, the navigation device 112 may identify that if a particular location 118 is selected, an adjustment of the route of the user 102 to arrive at a selected location at a time that is before the timing window. If such a n adjustment involves a reversal along the route that is not involved in the adjustment of the route at the first time (e.g., if navigating to the location 118 without having to backtrack along the route 106 entails a selection of the location 118 in advance of the timing window 202 in order to take the proper exit 420), the navigation device 112 may present the location 118 to the user 102 during the first time before the timing window.

Figure 11:
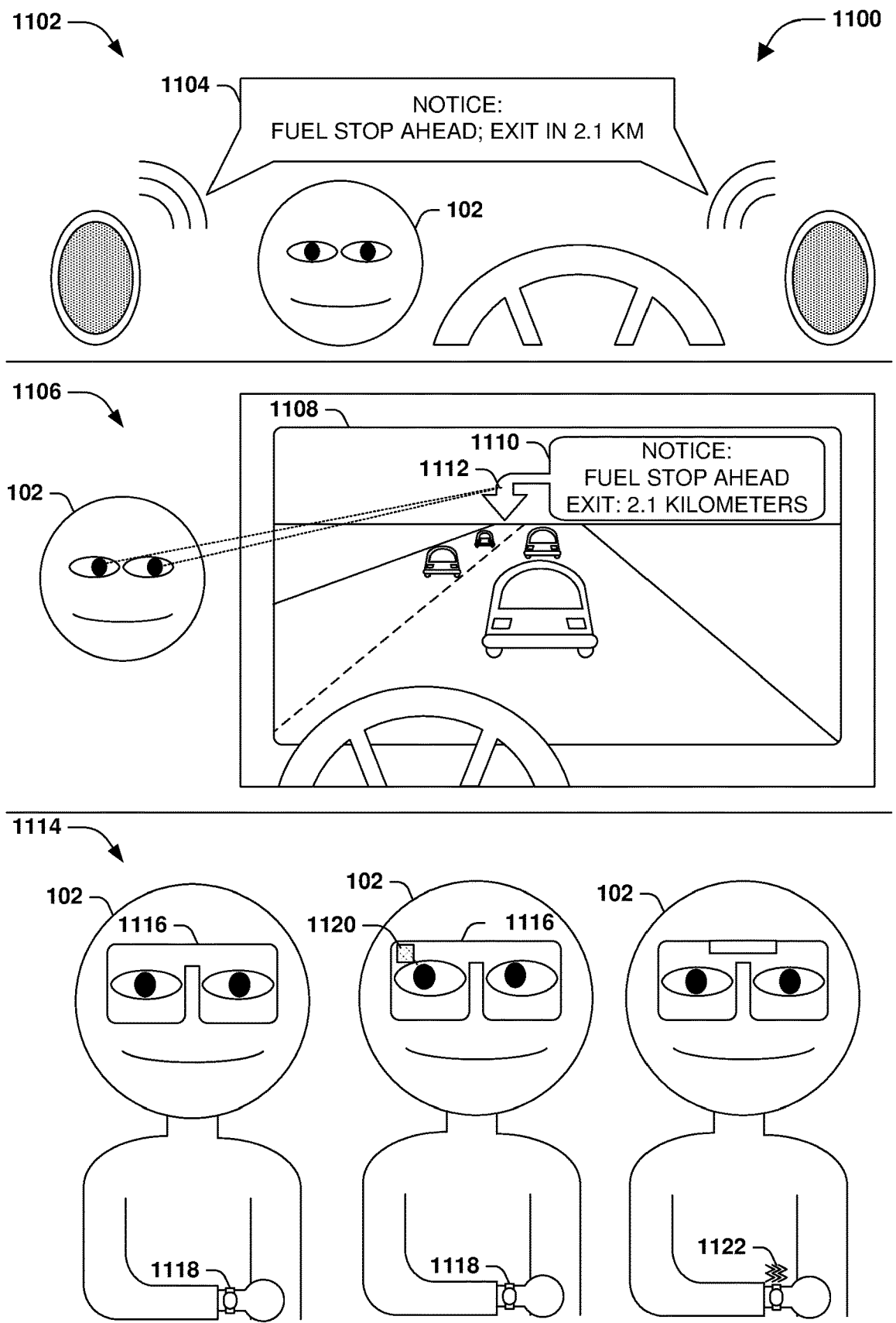
FIG. 11 is an illustration of an example technique for notifying a user about query results of a location query, in accordance with the techniques presented herein.

FIG. 11 presents an illustration of a set of exemplary scenarios 1100 whereby a navigation device 112 may notify the user 102 about a location 118 that fulfills a location query 114 and that is within a timing window 202 along a predicted route 106. As a first such example, a visual and/or audial indicator may be presented to the user 102 by the navigation device 112, such as a light on the dashboard of the vehicle 104 or an audio or voice cue 1104 prompting the user to take a particular exit 420 to arrive at a selected location 118. As a second such example, a visual indicator 1110 may be presented on a window 1108 of the vehicle 104, and, optionally, may be presented at a selected location 1114 on the window 1108 that correlates the visual indicator 1110 with the location 1112 of the location 118 through the window 1108 from the perspective of the user 102 (e.g., presenting a visual arrow and/or highlighting the location, when viewed through the window 1108 by the user 102, of an exit 420 to be taken to arrive at the location 118). As a third such example, the user 102 may wear one or more wearable devices while operating the vehicle 104, such as a pair of eyeglasses 1116 or a wristwatch 1118. The presentation of a notification of the selected location 118 through such wearable devices, e.g., by presenting a visual indicator 1120 within the viewable region of the eyeglasses 1116 worn by the user 102, and/or issuing a vibration alert 1122 through the wristwatch 1118 of the user 102 to indicate the arrival of the location 118 (e.g., flashing a leftward visual indicator 1120 or a vibration alert 1122 on the user's left wrist to draw the user's attention to the exit ramp 420 that the user 102 is to take to arrive at the location 118).

As a fourth variation of this fourth aspect, a navigation device 112 may respond to the selection of a location 118 by the user 102 in a variety of ways. As a first such example, the navigation device 112 may, upon receiving from the user 102 a selection 1002 of a selected location 118, choose the route 106 associated with the selected location 106 as a current route of the transit of the vehicle 104 (e.g., among a set of candidate routes, the navigation device 112 may identify the candidate route involving the selected location 118 as the current route of the vehicle 104). As a second such example, the navigation device 112 may, for the respective locations 118, identify a route adjustment of the route to include the current location 108, and present the route adjustment of the current location 108 along with the respective locations 118 (e.g., notifying the user 102 of the variation in the route 106, such as an updated estimated time of arrival at the destination of the route 106). As a third such example, the navigation device 112 may, upon receiving from the user 102 a selection 1002 of a selected location 118, notify the selected location 118 of the transit of the user 102 to the selected location 118 (e.g., contacting a selected restaurant to initiate a reservation). Many such variations may be included to utilize the selection 1002 of a selected location 118 in accordance with the techniques presented herein.

F. Computing Environment

Figure 12:
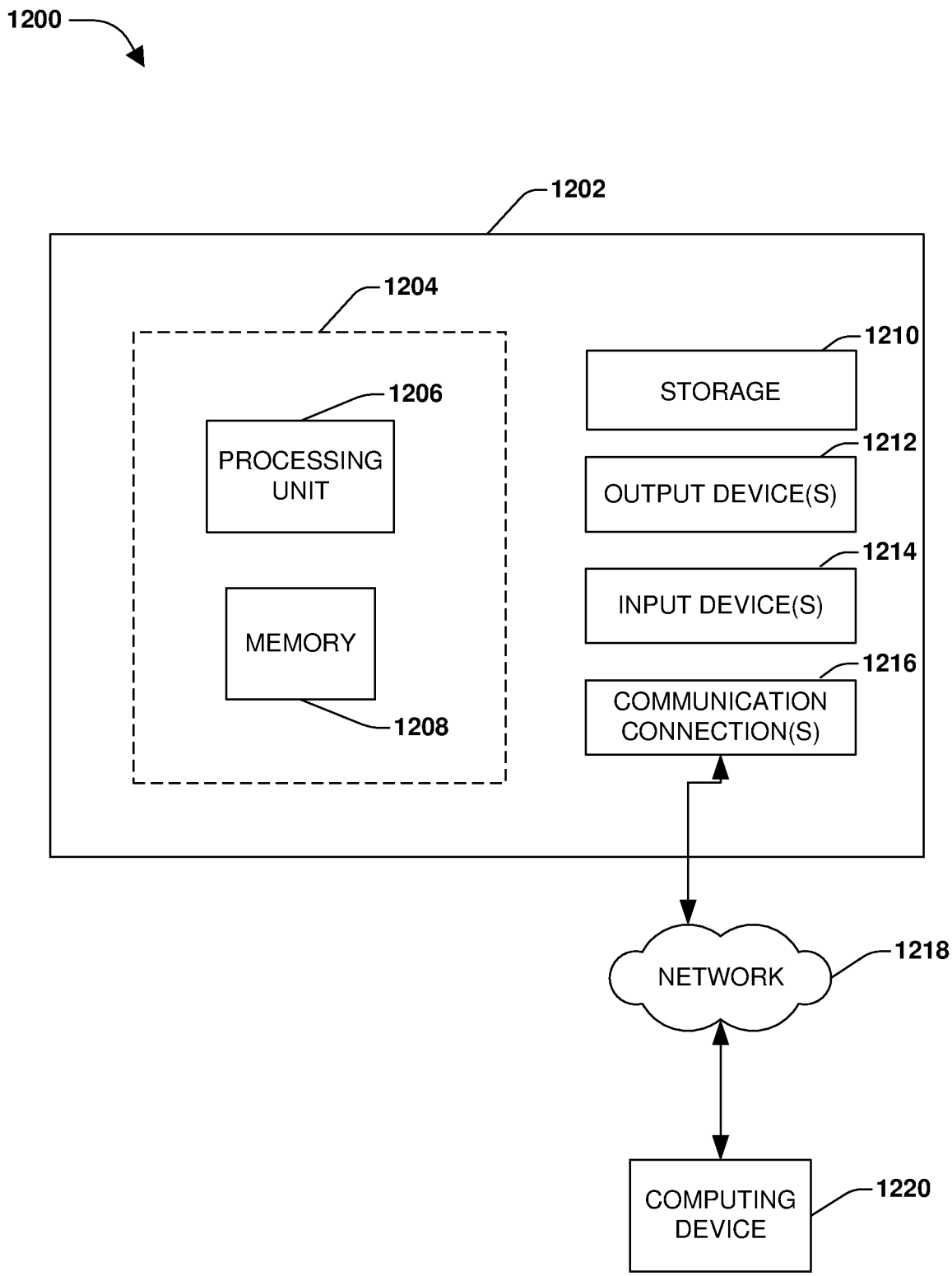
FIG. 12 is an illustration of an example computing environment wherein one or more of the provisions set forth herein may be implemented.

FIG. 12 and the following discussion provide a brief, general description of a suitable computing environment to implement embodiments of one or more of the provisions set forth herein. The operating environment of FIG. 12 is only one example of a suitable operating environment and is not intended to suggest any limitation as to the scope of use or functionality of the operating environment. Example computing devices include, but are not limited to, personal computers, server computers, hand-held or laptop devices, mobile devices (such as mobile phones, Personal Digital Assistants (PDAs), media players, and the like), multiprocessor systems, consumer electronics, mini computers, mainframe computers, distributed computing environments that include any of the above systems or devices, and the like.

Although not required, embodiments are described in the general context of "computer readable instructions" being executed by one or more computing devices. Computer readable instructions may be distributed via computer readable media (discussed below). Computer readable instructions may be implemented as program modules, such as functions, objects, Application Programming Interfaces (APIs), data structures, and the like, that perform particular tasks or implement particular abstract data types. Typically, the functionality of the computer readable instructions may be combined or distributed as desired in various environments.

FIG. 12 illustrates an example of a system 1200 comprising a computing device 1202 configured to implement one or more embodiments provided herein. In one configuration, computing device 1202 includes at least one processing unit 1206 and memory 1208. Depending on the exact configuration and type of computing device, memory 1208 may be volatile (such as RAM, for example), non-volatile (such as ROM, flash memory, etc., for example) or some combination of the two. This configuration is illustrated in FIG. 12 by dashed line 1204.

In other embodiments, device 1202 may include additional features and/or functionality. For example, device 1202 may also include additional storage (e.g., removable and/or non-removable) including, but not limited to, magnetic storage, optical storage, and the like. Such additional storage is illustrated in FIG. 12 by storage 1210. In one embodiment, computer readable instructions to implement one or more embodiments provided herein may be in storage 1210. Storage 1210 may also store other computer readable instructions to implement an operating system, an application program, and the like. Computer readable instructions may be loaded in memory 1208 for execution by processing unit 1206, for example.

The term "computer readable media" as used herein includes computer storage media. Computer storage media includes volatile and nonvolatile, removable and non-removable media implemented in any method or technology for storage of information such as computer readable instructions or other data. Memory 1208 and storage 1210 are examples of computer storage media. Computer storage media includes, but is not limited to, RAM, ROM, EEPROM, flash memory or other memory technology, CD-ROM, Digital Versatile Disks (DVDs) or other optical storage, magnetic cassettes, magnetic tape, magnetic disk storage or other magnetic storage devices, or any other medium which can be used to store the desired information and which can be accessed by device 1202. Any such computer storage media may be part of device 1202.

Device 1202 may also include communication connection(s) 1216 that allows device 1202 to communicate with other devices. Communication connection(s) 1216 may include, but is not limited to, a modem, a Network Interface Card (NIC), an integrated network interface, a radio frequency transmitter/receiver, an infrared port, a USB connection, or other interfaces for connecting computing device 1202 to other computing devices. Communication connection(s) 1216 may include a wired connection or a wireless connection. Communication connection(s) 1216 may transmit and/or receive communication media.

The term "computer readable media" may include communication media. Communication media typically embodies computer readable instructions or other data in a "modulated data signal" such as a carrier wave or other transport mechanism and includes any information delivery media. The term "modulated data signal" may include a signal that has one or more of its characteristics set or changed in such a manner as to encode information in the signal.

Device 1202 may include input device(s) 1214 such as keyboard, mouse, pen, voice input device, touch input device, infrared cameras, video input devices, and/or any other input device. Output device(s) 1212 such as one or more displays, speakers, printers, and/or any other output device may also be included in device 1202. Input device(s) 1214 and output device(s) 1212 may be connected to device 1202 via a wired connection, wireless connection, or any combination thereof. In one embodiment, an input device or an output device from another computing device may be used as input device(s) 1214 or output device(s) 1212 for computing device 1202.

Components of computing device 1202 may be connected by various interconnects, such as a bus. Such interconnects may include a Peripheral Component Interconnect (PCI), such as PCI Express, a Universal Serial Bus (USB), firewire (IEEE 1394), an optical bus structure, and the like. In another embodiment, components of computing device 1202 may be interconnected by a network. For example, memory 1208 may be comprised of multiple physical memory units located in different physical locations interconnected by a network.

Those skilled in the art will realize that storage devices utilized to store computer readable instructions may be distributed across a network. For example, a computing device 1220 accessible via network 1218 may store computer readable instructions to implement one or more embodiments provided herein. Computing device 1202 may access computing device 1220 and download a part or all of the computer readable instructions for execution. Alternatively, computing device 1202 may download pieces of the computer readable instructions, as needed, or some instructions may be executed at computing device 1202 and some at computing device 1220.

G. Usage of Terms

Although the subject matter has been described in language specific to structural features and/or methodological acts, it is to be understood that the subject matter defined in the appended claims is not necessarily limited to the specific features or acts described above. Rather, the specific features and acts described above are disclosed as example forms of implementing the claims.

As used in this application, the terms "component," "module," "system", "interface", and the like are generally intended to refer to a computer-related entity, either hardware, a combination of hardware and software, software, or software in execution. For example, a component may be, but is not limited to being, a process running on a processor, a processor, an object, an executable, a thread of execution, a program, and/or a computer. By way of illustration, both an application running on a controller and the controller can be a component. One or more components may reside within a process and/or thread of execution and a component may be localized on one computer and/or distributed between two or more computers.

Furthermore, the claimed subject matter may be implemented as a method, apparatus, or article of manufacture using standard programming and/or engineering techniques to produce software, firmware, hardware, or any combination thereof to control a computer to implement the disclosed subject matter. The term "article of manufacture" as used herein is intended to encompass a computer program accessible from any computer-readable device, carrier, or media. Of course, those skilled in the art will recognize many modifications may be made to this configuration without departing from the scope or spirit of the claimed subject matter.

Various operations of embodiments are provided herein. In one embodiment, one or more of the operations described may constitute computer readable instructions stored on one or more computer readable media, which if executed by a computing device, will cause the computing device to perform the operations described. The order in which some or all of the operations are described should not be construed as to imply that these operations are necessarily order dependent. Alternative ordering will be appreciated by one skilled in the art having the benefit of this description. Further, it will be understood that not all operations are necessarily present in each embodiment provided herein.

Moreover, the word "example" is used herein to mean serving as an example, instance, or illustration. Any aspect or design described herein as "example" is not necessarily to be construed as advantageous over other aspects or designs. Rather, use of the word example is intended to present concepts in a concrete fashion. As used in this application, the term "or" is intended to mean an inclusive "or" rather than an exclusive "or". That is, unless specified otherwise, or clear from context, "X employs A or B" is intended to mean any of the natural inclusive permutations. That is, if X employs A; X employs B; or X employs both A and B, then "X employs A or B" is satisfied under any of the foregoing instances. In addition, the articles "a" and "an" as used in this application and the appended claims may generally be construed to mean "one or more" unless specified otherwise or clear from context to be directed to a singular form.

Also, although the disclosure has been shown and described with respect to one or more implementations, equivalent alterations and modifications will occur to others skilled in the art based upon a reading and understanding of this specification and the annexed drawings. The disclosure includes all such modifications and alterations and is limited only by the scope of the following claims. In particular regard to the various functions performed by the above described components (e.g., elements, resources, etc.), the terms used to describe such components are intended to correspond, unless otherwise indicated, to any component which performs the specified function of the described component (e.g., that is functionally equivalent), even though not structurally equivalent to the disclosed structure which performs the function in the herein illustrated example implementations of the disclosure. In addition, while a particular feature of the disclosure may have been disclosed with respect to only one of several implementations, such feature may be combined with one or more other features of the other implementations as may be desired and advantageous for any given or particular application. Furthermore, to the extent that the terms "includes", "having", "has", "with", or variants thereof are used in either the detailed description or the claims, such terms are intended to be inclusive in a manner similar to the term "comprising."

What is claimed is:

1. A method, comprising:
   identifying a transit contingency corresponding to historic times and frequencies at which a user has performed an action;
   predicting a route of a vehicle and a projected location of the vehicle along the route during a time window corresponding to the transit contingency and a location query for locations;
   identifying a list of locations that satisfy the location query and that are within a proximity range of the projected location;
   preferentially sorting and filtering the list of locations based upon one or more factors to generate a sorted and filtered list of locations, wherein a first location is excluded from the list of locations based upon a first factor indicating that the user dislikes an aspect of the first location;
   generating query results comprising the sorted and filtered list of locations that excludes the first location; and
   presenting the query results, as the sorted and filtered list of locations, for the location query.

2. The method of claim 1, wherein preferentially sorting and filtering comprises:
   removing a second location from the list of locations based upon a second factor.

3. The method of claim 1, comprising:
   identifying within a user profile of the user of the vehicle a future destination of the user that is consistent with a current transit of the vehicle; and
   predicting the route based upon the future destination.

4. The method of claim 1, wherein the location query is associated with an operating metric of the vehicle.

5. The method of claim 1, comprising:
   parsing the location query to identify a user-specified time window as the time window.

6. The method of claim 1, comprising:
   evaluating an operating metric of the vehicle to determine the time window.

7. The method of claim 1, comprising:
   identifying the time window to reflect the transit contingency of a current transit of the vehicle.

8. The method of claim 1, comprising:
   sorting and filtering the list of locations based upon user preferences indicating preferences and dislikes of the user.

9. The method of claim 1, comprising:
   identifying a set of routes that satisfy the location query and that are within a proximity range of the projected location.

10. The method of claim 9, comprising:
    sorting the set of routes based upon probabilities that routes within the set of routes will be traveled by the vehicle.

11. The method of claim 7, comprising:
    identifying the transit contingency as a time at which the user associated with the vehicle performs an action.

12. The method of claim 7, comprising:
    identifying the transit contingency as a frequency at which the user associated with the vehicle performs an action.

13. A computing device, comprising:
    a processor; and
    a memory storing instructions that, when executed by the processor, cause the processor to:
      identify a transit contingency corresponding to historic times and frequencies at which a user has performed an action;
      predict a route of a vehicle and a projected location of the vehicle along the route during a time window corresponding to the transit contingency and a location query for locations;
      identify a list of locations that satisfy the location query and that are within a proximity range of the projected location;

preferentially sort and filter the list of locations based upon one or more factors to generate a sorted and filtered list of locations, wherein a first location is excluded from the list of locations based upon a first factor indicating that the user dislikes an aspect of the first location;

generate query results comprising the sorted and filtered list of locations that excludes the first location; and present the query results, as the sorted and filtered list of locations, for the location query.

14. The computing device of claim 13, wherein the instructions cause the processor to:

sort the list of locations based upon a user preference.

15. The computing device of claim 14, wherein the instructions cause the processor to:

remove a location from the list of locations based upon the location having an operating time window that does not overlap with the time window of the location query.

16. The computing device of claim 13, wherein the instructions cause the processor to:

obtain a set of query results for the location query; and sort the set of query results based upon a user popularity of locations within the set of query results among users in transit along at least a portion of the route of the vehicle.

17. A non-transitory computer-readable medium comprising processor-executable instructions configured to:

identify a transit contingency corresponding to historic times and frequencies at which a user has performed an action;

predict a route of a vehicle and a projected location of the vehicle along the route during a time window corresponding to the transit contingency and a location query for locations;

identify a list of locations that satisfy the location query and that are within a proximity range of the projected location;

preferentially sort and filter the list of locations based upon one or more factors to generate a sorted and filtered list of locations, wherein a first location is excluded from the list of locations based upon a first factor indicating that the user dislikes an aspect of the first location;

generate query results comprising the sorted and filtered list of locations that excludes the first location; and present the query results, as the sorted and filtered list of locations, for the location query.

18. The non-transitory computer-readable medium of claim 17, comprising instructions configured to:

compare a current location of the vehicle for predicting the route by comparing a current transit of the vehicle with historical routes previously completed by vehicles.

19. The non-transitory computer-readable medium of claim 17, comprising instructions configured to:

identify within a user profile of the user of the vehicle a future destination of the user that is consistent with a current transit of the vehicle; and predict the route based upon the future destination.

20. The non-transitory computer-readable medium of claim 17, wherein the location query is associated with an operating metric of the vehicle.

* * * * *